United States Patent
Zhang et al.

(10) Patent No.: US 10,874,609 B2
(45) Date of Patent: Dec. 29, 2020

(54) ß-CYCLODEXTRIN-BASED STAR-SHAPED POLYMER, A PREPARATION METHOD THEREFOR AND AN INTEGRATED UNIMOLECULAR MICELLE SYSTEM FOR DIAGNOSIS AND TREATMENT THEREOF

(71) Applicant: South China University of Technology, Guangzhou (CN)

(72) Inventors: Lijuan Zhang, Guangzhou (CN); Wenjing Lin, Guangzhou (CN); Na Yao, Guangzhou (CN); Xiaofang Zhang, Guangzhou (CN)

(73) Assignee: South China University of Technology

( * ) Notice: Subject to any disclaimer, the term of this patent is extended or adjusted under 35 U.S.C. 154(b) by 161 days.

(21) Appl. No.: 16/080,355

(22) PCT Filed: Dec. 14, 2016

(86) PCT No.: PCT/CN2016/109907
§ 371 (c)(1),
(2) Date: Aug. 28, 2018

(87) PCT Pub. No.: WO2017/173846
PCT Pub. Date: Oct. 12, 2017

(65) Prior Publication Data
US 2019/0380959 A1 Dec. 19, 2019

(30) Foreign Application Priority Data

Apr. 5, 2016 (CN) .......................... 2016 1 0210456

(51) Int. Cl.
*A61K 9/107* (2006.01)
*A61K 47/14* (2017.01)
(Continued)

(52) U.S. Cl.
CPC ............ *A61K 9/1075* (2013.01); *A61K 47/14* (2013.01); *A61K 47/22* (2013.01); *A61K 47/34* (2013.01);
(Continued)

(58) Field of Classification Search
CPC ...... A61K 9/1075; A61K 47/40; A61K 47/34; A61K 47/22; A61K 47/14; A61K 45/06;
(Continued)

(56) References Cited

U.S. PATENT DOCUMENTS

2004/0170595 A1 9/2004 Zhao
2006/0024264 A1 2/2006 Kuroda et al.

FOREIGN PATENT DOCUMENTS

| CN | 102702453 A | 10/2012 |
|---|---|---|
| CN | 102702454 A | 10/2012 |

(Continued)

OTHER PUBLICATIONS

Machine translation of CN103396521A (Year: 2013).*
(Continued)

*Primary Examiner* — Aradhana Sasan
*Assistant Examiner* — Quanglong N Truong
(74) *Attorney, Agent, or Firm* — The Webb Law Firm

(57) ABSTRACT

Disclosed is a β-cyclodextrin-based star-shaped polymer and a preparation method therefor, and an integrated unimolecular micelle system for diagnosis and treatment based on the star-shaped polymer and the use thereof. The polymer has a structure represented by the following formula (I):

(Continued)

(I)

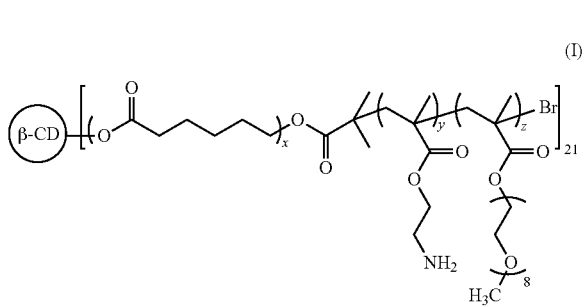

wherein x=4-15, y=3-20, and z=10-30.

10 Claims, 11 Drawing Sheets

(51) Int. Cl.
A61K 47/22 (2006.01)
A61K 47/34 (2017.01)
A61K 47/40 (2006.01)
A61K 31/704 (2006.01)
A61K 45/06 (2006.01)

(52) U.S. Cl.
CPC .......... A61K 47/40 (2013.01); A61K 31/704 (2013.01); A61K 45/06 (2013.01)

(58) Field of Classification Search
CPC .... A61K 31/704; A61K 33/24; A61K 47/183; A61K 47/50; A61K 49/04; C08G 63/08; C08F 293/00; C08F 220/34; C08F 220/28; C08F 220/343; C08F 220/286; C08F 8/12
See application file for complete search history.

(56) References Cited

FOREIGN PATENT DOCUMENTS

| CN | 103396521 A | 11/2013 |
| CN | 104224714 A | 12/2014 |
| CN | 105017445 A | 11/2015 |
| CN | 105778021 A | 7/2016 |
| TW | 200621268 | 7/2006 |

OTHER PUBLICATIONS

Machine translation of CN102702453B (Year: 2012).*
Chen et al., "Functionalized Amphiphilic Hyperbranched Polymers for Targeted Drug Delivery", Biomacromolecules, 2008, pp. 2578-2585, vol. 9.
Peng et al., "PEGylated dendrimer-entrapped gold nanoparticles for in vivo blood pool and tumor imaging by computed tomography", Biomaterials, 2012, pp. 1107-1119, vol. 33.
Prabaharan et al., "Folate-conjugated amphiphilic hyperbranched block copolymers based on Boltorn @ H40, poly(L-lactide) and poly(ethylene glycol) for tumor-targeted drug delivery", Biomaterials, 2009, pp. 3009-3019, vol. 30.
Thoma et al., "Cationic Methacrylate Polymers as Topical Antimicrobial Agents against Staphylococcus aureus Nasal Colonization", 2014, Biomacromolecules, pp. 2933-2943, vol. 15.
Wen et al., "Multifunctional dendrimer-entrapped gold nanoparticles for dual mode CT/MR imaging applications", Biomaterials, 2013, pp. 1570-1580, vol. 34.
Yao et al., "Amphiphilic b-Cyclodextrin-Based Star-Like Block Copolymer Unimolecular Micelles for Facile in Situ Preparation of Gold Nanoparticles", Journal of Polymer Science, 2016, pp. 186-196, vol. 54.
Zhu et al., "Cationic Methacrylate Copolymers Containing Primary and Tertiary Amino Side Groups: Controlled Synthesis via RAFT Polymerization, DNA Condensation, and In Vitro Gene Transfection", Journal of Polymer Science, 2010, pp. 2869-2877, vol. 48.

* cited by examiner

β-CYCLODEXTRIN-BASED STAR-SHAPED POLYMER, A PREPARATION METHOD THEREFOR AND AN INTEGRATED UNIMOLECULAR MICELLE SYSTEM FOR DIAGNOSIS AND TREATMENT THEREOF

FIELD OF THE INVENTION

The invention belongs to the technical field of biological medical polymer materials, in particular relates to an amphiphilic pH-responsive β-cyclodextrin-based star-shaped polymer and a preparation method therefor, and an integrated unimolecular micelle system for diagnosis and treatment based on the star-shaped polymer and application thereof.

BACKGROUND OF THE ART

With the continuous increase in the incidence of tumors, tumors are becoming more and more painful to humans. It is very difficult to find tumors early, and after the diagnosis is made, treatments that are supposed to be effective cannot fully realize their function. Although nano-based carriers developed from the four major classes of materials including liposomes, polymers, albumin, and nanocrystals are approved and used in clinics, they are only used in treatment. Therefore, how to achieve early diagnosis and treatment of tumors with high-efficiency and low-toxicity has become an urgent problem in clinical practice. The development and research of drug nanocarriers have brought new ideas and conceptual changes to the pharmaceutical industry. One of them is the preparation and realization of a multi-functional single drug nanocarrier, which integrates therapy and diagnosis. These multi-functional theranostic nanocarriers that are available for molecular targeting, imaging, and controlled-release drugs can convey the imaging agent together with anti-tumor drugs to the lesion site specifically for early diagnosis and targeted therapy of the tumor. They can also control the release of drugs, avoid damage to normal tissue, reasonably improve drug availability and detect the condition of the lesion site, so as to provide patients with a safer, less toxic and effective treatment.

The nano drug delivery system combines the advantages of constant circulation, targeting, controlled release, transmucosal, transdermal, and physical response to overcome the shortcomings of existing drugs including low bioavailability, poor stability, short pharmacological action time, and severe side effect, etc. Various structures of functional polymeric nanovectors, including linear, star-shaped, branched and dendritic polymers, along with their self-assembled polymer aggregates (e.g. micelles and vesicles), have been developed to improve water solubility, controlled release of drugs, and the aggregation at the tumor tissue. Among the above carriers, linear polymers have attracted significant attention for their template flexibility and tunable loading capacity. However, multimolecular micelle system may disassemble into unimers, leading to the burst-release of loaded drugs. In addition, the micelle particle size is typically around 100-500 nm, which limits their effectiveness in drug delivery. Unimolecular micelles (micelles composed of a single copolymer) present one promising solution to the above problems including self-dissembling and oversize particle. Composed of only one polymer molecule in each micelle, the unimolecular micelle has stable structure, which is insensitive to concentration, temperature and pH, etc. Moreover, its hydrophobic and hydrophilic composition and micelle particle size can be flexibly adjusted, so that as a nanoreactor, a series of therapeutic molecules with uniform particle size distribution can be obtained in it and be effectively delivered. For instance, Chen et al. have synthesized H40-poly(caprolactone)-b-poly(ethylene glycol)-folic acid (H40-PCL-b-PEG-FA) by ring-opening polymerization (ROP) and end group coupling on the surface of H40 to study the entrapment and release of anticancer drugs 5-fluorouracil (5-FU) and paclitaxel (PTX) in unimolecular micelles (Biomacromolecules, 2008, 9: 2578-2585). Gong's group have developed unimolecular micelles formed by H40-poly(lactic acid)-b-poly(ethylene glycol-folate) (H40-PLA-b-PEG-OH/FA) and explored how they deliver anticancer drugs 5-FU and doxorubicin (DOX) and poison cancer cells (Biomaterials, 2009, 30: 3009-3019). Patent application CN201410483558.X disclosed a folate receptor-mediated self-assembled unimolecular micelle with a formulation of H40-PLGA-MPEG/PEG-FA and a preparation method therefor, utilizing the active targeting function of folic acid to realize controlled release of drug at the tumor site.

Molecules used for cancer diagnosis and treatment include quantum dots, magnetic nanoparticles, gold/silver nanoparticles, lipid/polymer nanoparticles, and mesoporous nanomaterials. Gold nanoparticles (AuNPs) are nano-sized gold particles with different properties according to different experimental conditions using gold metal salts as raw materials. AuNPs possess good biocompatibility, can be easily synthesized and modified, have controllable size and good monodispersity, which make it an attractive choice for drug delivery, gene delivery, and CT imaging. It is worth-mentioning that FDA has approved the use of AuNPs for cancer diagnosis, which further proves its relatively good biosafety. In particular, the X-ray attenuation of 30 nm gold nanoparticles (120 kVp) is 5.7 times faster than that of the conventional iodine-based contrast agent Omnipaque, which theoretically provides better CT imaging efficacy, thus could make the clinical diagnosis of disease more convenient and bring convenience for the patient. Peng et al. mainly studied the template of dendrimer and the properties of stable nanoparticles, using $G5.NH_2-mPEG_{20}$ as a template to synthesize fifth-generation dendrimer-encapsulated AuNPs. They showed that gold nanoparticles could be used as a highly effective contrast agent for CT imaging (Biomaterials, 2012, 33: 1107-1119). Wen Shihui et al. of the same group modified gadolinium (Gd) chelators on $G5.NH_2-mPEG_{20}$ and used the modified molecules as templates to synthesize Gd—Au-DENPs, which can be used for CT/MR dual imaging (Biomaterials, 2013, 34: 1570-1580). However, these studies did not discuss whether the structure of the polymer carrier used is stable, and which factors regulate the size and morphology of the AuNPs. Moreover, there are no papers and patents reporting unimolecular micelles as templates to simultaneously load AuNPs and anticancer drugs for the treatment and diagnosis of tumors.

SUMMARY OF THE INVENTION

In order to overcome the disadvantages and deficiencies described above, the primary purpose of the invention is to provide an amphiphilic pH-responsive β-cyclodextrin-based star-shaped polymer. The structure of the polymer is: β-cyclodextrin, hydrophobic ε-caprolactone, pH-responsive 2-aminoethyl methacrylate, and hydrophilic poly(ethylene glycol) methyl ether methacrylate sequentially polymerized to obtain amphiphilic pH response star-shaped polymer.

Another purpose of the invention is to provide a method for preparing the aforementioned amphipathic pH-responsive β-cyclodextrin-based star-shaped polymer. This method firstly synthesizes the precursor of the pH-responsive monomer 2-aminoethyl methacrylate (AEMA), tert-butyl carbamate (tBAM), using tert-butyl N-(2-hydroxyethyl)carbamate and methacryloyl chloride; 21-arm β-CD is used to initiate ring-opening polymerization (ROP) of ε-caprolactone to obtain β-CD-(PCL-OH)$_{21}$, then an acylating agent is used to acylate all the end group of β-CD-(PCL-OH)$_{21}$ to obtain macroinitiator β-CD-(PCL-Br)$_{21}$; then this macroinitiator is used to initiate the polymerization of tBAM and the hydrophilic monomer poly(ethylene glycol) methyl ether methacrylate (PEGMA) through activators regenerated by electron transfer atom transfer radical polymerization (ARGET ATRP); finally, the tert-butyl ester groups on tBAM are selectively hydrolyzed to obtain the final polymer β-CD-(PCL-b-PAEMA-b-PPEGMA)$_{21}$ containing AEMA.

Another purpose of the invention is to provide a unimolecular micelle system based on the amphiphilic pH responsive β-cyclodextrin-based star-shaped polymer. The amphipathic pH-responsive β-cyclodextrin-based star-shaped-shaped polymer of the present invention could be dissolved in a solvent to prepare a nano-unimolecular micelle system with an inner layer of hydrophobic blocks linked by β-cyclodextrin, a middle layer of pH-responsive blocks, and a hydrophilic shell.

A further purpose of the invention is to provide the application of the above-mentioned unimolecular micelle system in loading water-insoluble drugs.

Yet another purpose of the invention is to provide an AuNPs-loaded composite material based on the above-mentioned unimolecular micelle system. In the amphipathic pH-responsive β-cyclodextrin-based star-shaped polymer of the present invention, the poly(2-aminoethyl methacrylate) (PAEMA) segment is hydrophilic and cationic. It can also serve as reducing agent and capturing agent to capture gold ions, reduce them to gold atoms in situ, and finally form stable gold nanoparticles due to its primary amine groups, in which the lone pair electrons on N atom are coordinatively reducing.

Still another purpose of the invention is to provide the application of the above-described stable AuNPs-loaded composite material in CT imaging.

Still another purpose of the invention is to provide the application of the above-described AuNPs-loaded composite material in loading water-insoluble drugs, especially in loading anticancer drugs (like DOX). Under weakly acidic conditions (pH 5-6.5) of the tumor tissue, the pH-responsive group is protonated to be hydrophilic and the micelle swells, resulting in rapid, controlled release of the entrapped drug. If the entrapped drug contains an amino group (such as DOX), protonation of the amino group will increase the drug's solubility and accelerate its diffusion, which is another important factor for controlled release of the drug. This structurally stable unimolecular micelle nanocarrier can simultaneously achieve tumor drug delivery and CT imaging, which effectively realizes its practical value in an integrated system for diagnosis and treatment.

The purpose of the invention is achieved by the following scheme:

An amphipathic pH-responsive β-cyclodextrin-based star-shaped polymer with the structure represented by the following formula (I):

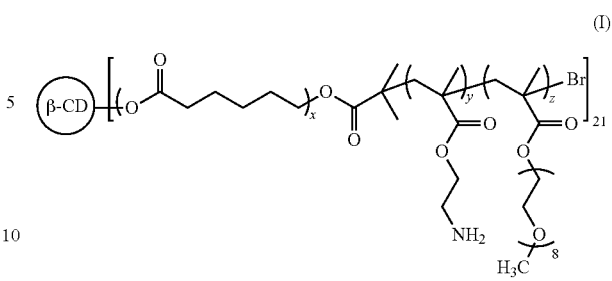

Wherein x=4~15, y=3~20, z=10~30.

The amphipathic pH-responsive β-cyclodextrin-based star-shaped polymer of the present invention is designated as β-CD-(PCL-b-PAEMA-b-PPEGMA)$_{21}$.

Preferably, the amphiphilic pH-responsive β-cyclodextrin-based star-shaped polymer of the invention has a number average molecular weight of 144922-364141 g/mol.

The invention provides a preparation method of the amphipathic pH-responsive β-cyclodextrin-based star-shaped polymer, comprising the following specific steps:

(1) preparation of a pH-responsive monomer precursor (tBAM), wherein tert-butyl N-(2-hydroxyethyl)carbamate, N,N-diisopropylethylamine are mixed in a solvent, and methacryloyl chloride is added under ice bath condition; the reaction is carried out under ice bath condition and subsequently at room temperature to obtain the precursive pH-responsive monomer t-butyl methacrylate-2-carbamate (tBAM);

(2) preparation of a polymer containing polycaprolactone β-CD-(PCL-OH)$_{21}$, wherein β-CD, ε-CL and a catalyst are mixed and heated to react, so as to obtain the polymer 13-CD-(PCL-OH)$_{21}$;

(3) preparation of a macroinitiator β-CD-(PCL-Br)$_{21}$, wherein the β-CD-(PCL-OH)$_{21}$ prepared in step (2) is dissolved in a solvent; Then triethylamine (TEA) and initiator 2-bromoisobutyryl bromide (BIBB) are added under ice bath; the reaction is carried out under ice bath condition and subsequently at room temperature to obtain the macroinitiator β-CD-(PCL-Br)$_{21}$;

(4) preparation of a pH-responsive polymer precursor β-CD-(PCL-b-PtBAM)$_{21}$: the macroinitiator β-CD-(PCL-Br)$_{21}$ prepared in step (3), the precursor tBAM prepared in step (1) and a catalyst are dissolved in a solvent, after which a ligand 1,1,4,7,10,10-hexamethyltriethylenetetramine (HMTETA) is further added; then a reducing agent is introduced and the solution is heated to react to obtain the pH-responsive polymer β-CD-(PCL-b-PtBAM)$_{21}$;

(5) preparation of an amphipathic star-shaped polymer β-CD-(PCL-b-tBAM-b-PPEGMA)$_{21}$, wherein the pH-responsive polymer precursor β-CD-(PCL-b-PtBAM)$_{21}$ prepared in step (4), poly(ethylene glycol) methyl ether methacrylate (PEGMA), a ligand 1,1,4,7,10,10-hexamethyltriethylenetetramine (HMTETA) and a catalyst are dissolved in a solvent; after mixing homogeneously, a reducing agent is added and the solution is heated to react to obtain the amphipathic star-shaped polymer β-CD-(PCL-b-tBAM-b-PPEGMA)$_{21}$;

(6) preparation of an amphipathic pH-responsive β-cyclodextrin-based star-shaped polymer β-CD-(PCL-b-PAEMA-b-PPEGMA)$_{21}$, wherein the amphipathic star-shaped polymer prepared in step (5) is dissolved in a solvent, and after addition of trifluoroacetic acid (TFA), the reaction is carried out under ice bath condition and subsequently at room temperature to obtain the amphipathic pH-responsive β-cyclodextrin-based star-shaped polymer β-CD-(PCL-b-PAEMA-b-PPEGMA)$_{21}$.

The molar parts of reactants in step (1) are as follows:

| | |
|---|---|
| Tert-butyl N-(2-hydroxyethyl)carbamate | 1 |
| N,N-diisopropylethylamine | 1-3 |
| Methacryloyl chloride | 1-3 |

The molar parts of reactants in step (2) are as follows:

| | |
|---|---|
| β-CD | 1 |
| ε-CL | 84-315 |

The molar parts of reactants in step (3) are as follows:

| | |
|---|---|
| β-CD-(PCL-OH)$_{21}$ | 1 |
| TEA | 21-84 |
| BIBB | 21-84 |

The molar parts of reactants in step (4) are as follows:

| | |
|---|---|
| Macroinitiator (β-CD-(PCL-Br)$_{21}$) | 1 |
| tBAM | 63-420 |
| HMTETA | 8-12 |

The molar parts of reactants in step (5) are as follows:

| | |
|---|---|
| pH-responsive polymer precursor | 1 |
| PEGMA | 210-630 |
| HMTETA | 8-12 |

The molar parts of reactants in step (6) are as follows:

| | |
|---|---|
| Amphipathic star-shaped polymer | 1 |
| TFA | 30-60 |

Preferably, in step (1) the reaction is carried out under ice bath condition for 0.5-4 h, and subsequently at room temperature for 24-48 h.

The solvent described in step (1) is used to provide a solution reaction environment, which may be an organic solvent commonly used in this field, such as dichloromethane.

Preferably, in step (2) the solution is heated to 90-130° C. to react for 24-48 h.

The catalyst in step (2) may be a commonly used catalyst in the field, such as Sn(Oct)$_2$, with a catalytic amount.

Preferably, in step (3) the reaction is carried out under ice bath condition for 4-6 h, and subsequently at room temperature for 24-48 h.

The solvent described in step (3) is used to provide a solution reaction environment, which may be an organic solvent commonly used in this field, such as tetrahydrofuran.

Preferably, in step (4) the solution is heated to 60-90° C. to react for 24-48 h.

Preferably, in step (5) the solution is heated to 60-90° C. to react for 48-96 h.

The catalysts described in steps (4) and (5) may be commonly used copper(II) catalysts in the art, such as CuBr$_2$, with a catalytic amount.

The reducing agents in steps (4) and (5) may be reducing agents commonly used in this field, such as Sn(Oct)$_2$ or ascorbic acid, and the amount thereof should be the same as the amount of the ligand.

The solvents described in steps (4) and (5) are used to provide a solution reaction environment, which may be organic solvents commonly used in this field, such as toluene.

Preferably, in step (6) the reaction is carried out under ice bath condition for 0.5-4 h, and subsequently at room temperature for 4-10 h.

The solvent described in step (6) is used to provide a solution reaction environment and may be an organic solvent commonly used in this field, such as dichloromethane.

Preferably, after the reaction in step (1) is completed, the reaction system is cooled, purified and dried to obtain a purified product. The purification preferably comprises of removing the solvent by rotary evaporation, sequentially extracting with water, glacial acetic acid, NaHCO$_3$ and NaCl solution, drying the resulting organic phase over Na$_2$SO$_4$ followed by filtering, and finally concentrating the eluate by rotary evaporation to obtain the purified product.

After the reaction in step (2) is completed, the reaction system is preferably cooled, purified and dried to obtain a purified product. The purification preferably comprises of removing the solvent by rotary evaporation, dissolving the product in tetrahydrofuran, and finally adding 10-fold volume of 0° C. water/methanol (1:1, v/v) to precipitate the product.

After the reaction of step (3) is completed, the reaction system is preferably purified and dried to obtain a purified product. The purification is preferably carried out by removing the quaternary ammonium salt from the reaction solution through a neutral alumina column, then removing most of the solvent by rotary evaporation, and finally adding 10-fold volume of 0° C. n-hexane to precipitate the product.

After the reactions in steps (4) and (5) are completed, the reaction systems are preferably cooled, purified and dried to obtain a purified product. The purification preferably comprises of dissolving the product in tetrahydrofuran, removing the catalyst through a neutral alumina column, conducting rotary evaporation and adding 10-fold volume of 0° C. n-hexane to precipitate the product.

After the reaction in step (6) is completed, the reaction system is preferably cooled, purified and dried to obtain a purified product. The purification is preferably carried out by dissolving the product in tetrahydrofuran, concentrating the solution by rotary evaporation, adding 10-fold volume of 0° C. n-hexane, drying overnight, washing with NaOH until pH=8.0, immediately placing the product in a dialysis bag for three days, and then lyophilizing it.

Preferably, the above reactions are carried out under inert gas protection and anhydrous conditions.

The invention also provides an amphipathic pH-responsive unimolecular micelle system based on the β-cyclodextrin star-shaped polymers described above. The micelle system is obtained by dissolving the amphiphilic pH-responsive β-cyclodextrin-based star-shaped polymer in a solvent.

The above-mentioned unimolecular micelle system could be applied to loading water-insoluble drugs.

The invention also provides an AuNPs-loaded composite material based on the above-mentioned unimolecular micelle system. After the amphiphilic pH-responsive β-cyclodextrin-based star-shaped polymer and the water-soluble gold salt are respectively dissolved in the same solvent, the amphiphilic pH-responsive β-cyclodextrin-based star-shaped polymer solution and the water-soluble gold salt solution are mixed and stirred to obtain a AuNPs-loaded composite material.

The water soluble gold salt may be chloroauric acid, etc.

After mixing and stirring, the mixture could be separated through filtration. A composite material is obtained after drying the residue. The solvent is preferably water.

The above AuNPs-loaded composite material of the invention could be applied to CT imaging.

The above-mentioned AuNPs-loaded composite could be used for loading water-insoluble drugs, and specifically comprises the following steps: dissolving a water-insoluble drug in an organic solvent; meantime dissolving the amphophilic pH-responsive β-cyclodextrin-based star-shaped polymer in the same organic solvent to obtain a unimolecular micelle system; then mixing the unimolecular micelle system with the water-insoluble drug solution, stirring homogeneously, and dialyzing to obtain a water-insoluble-drug-loaded micelle system.

The water-insoluble drug refers to a drug having a solubility of less than or equal to 1 g/L.

The organic solvent is preferably selected from dimethyl sulfoxide or dimethylformamide.

The water-insoluble-drug-loaded micelle system can control the loaded drug to release slowly in normal tissue (pH 7.4), and achieve rapid and controlled release at a weakly acidic condition of the tumor cells (pH 5 to 6.5).

The mechanism of the invention is:

The invention links β-cyclodextrin to the hydrophobic block ε-caprolactone (ε-CL), then polymerizes the pH-responsive/reducible block 2-aminoethyl methacrylate (AEMA), hydrophilic block poly(ethylene glycol) methyl ether methacrylate (PEGMA) in order. They are combined to obtain the amphipathic pH-responsive star-shaped polymer, which is dissolved in a solvent to obtain structurally stable unimolecular micelle with 21-arm-β-CD as the core, hydrophobic PCL as the inner layer, pH-responsive/reducible PAEMA as the middle layer, and hydrophilic PPEGMA as the outer shell. β-CD are readily available, biocompatible, non-toxic, and biodegradable. As the hydrophobic block, PCL hosts anticancer drugs. The PAEMA mesosphere with primary amine groups not only provides the coordination bonding with metal ions for preparation of stable AuNPs, but acts as a pH-responsive block to trigger drug release under weakly acidic tumor conditions by protonation. Nonimmunogenic, nonantigenic and nontoxic PEGMA is used as the hydrophilic shell and a compact protective layer that maintains the stability of the micelles during biological circulation. DOX, widely used for cancer treatment, is encapsulated in unimolecular micelles. The DOX-loaded micelles remain stable under neutral condition, while under the acidic tumor conditions, they release the drug rapidly due to the protonation of PAEMA and DOX. By adjusting the proportion of each block in the polymer, the release rate of the drug can be adjusted to meet the release requirements of different drugs. The amphiphilic pH-responsive star-shaped polymer structure can increase the pH-sensitivity of micelles, meantime maintaining a high drug loading content, which controls drug release more effectively, and improves the efficiency of drug treatment.

Compared with the existing technology, the present invention has the following advantages and beneficial effects:

(1) The preparation method of the invention is simple with mild reaction conditions. The degree of polymerization of each block of the amphipathic pH-responsive star-shaped polymer could be easily modulated, and the molecular weight could be adjusted within a relatively wide range.

(2) The amphipathic pH-responsive star-shaped polymer unimolecular micelle of the invention could be used to prepare in situ small-sized AuNPs.

(3) The amphiphilic pH-responsive star-shaped polymer unimolecular micelle of the invention could easily adjust the proportion of each block, and can be applied to the preparation of a water-insoluble-drug-loaded micelle system to meet the release requirements of different drugs.

(4) The amphiphilic pH response star-shaped polymer unimolecular micelle system of the invention can efficiently load AuNPs and hydrophobic drugs simultaneously, which combines tumor diagnosis and tumor chemotherapy, improves the treatment efficiency of cancer and provides valuable preparation technology for future integrated diagnostic and therapeutic systems.

DETAILED DESCRIPTION OF THE EMBODIMENTS

The present invention will be further described in detail with reference to the embodiments and drawings, which form a part hereof. But the embodiments of the invention are not meant to be limiting thereto.

The sources of reagents used in the following embodiments are all commercially available.

Embodiment 1: pH-Responsive Monomer Precursor (tBAM)

A 250 mL Schlenk flask was dried by a spirit lamp for 10 min. After cooling down, a magnetic stirring bar and tert-butyl N-(2-hydroxyethyl)carbamate (5 g, 31 mmol) were added to the flask, which was sealed by a rubber stopper. The flask was evacuated to vacuum and filled with argon for three times. Then under Ar atmosphere, 100 mL dichloromethane (DCM) and N,N-diisopropylethylamine (16.2 mL, 93 mmol) were added in sequence. Methacryloyl chloride (3.3 mL, 31 mmol) was further added dropwise under ice bath condition. The reaction was carried out at 0° C. for 4 h and then at room temperature for another 24 h. The mixture was extracted successively with water, 400 mL 10% citric acid, 400 mL saturated NaHCO$_3$ and 400 mL saturated NaCl. The organic phase was collected and dried through Na$_2$SO$_4$ followed by rotary evaporation to remove part of the solvent. The obtained white liquid was precipitated by n-hexane, filtered, and finally dried under vacuum (40° C., 35 mb) for 24 h to obtain the product.

Figure 1:
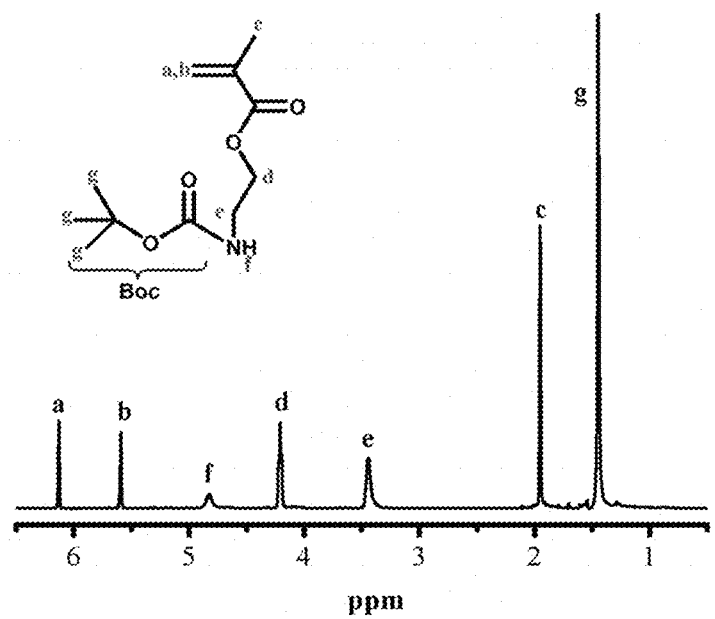
FIG. 1 is the $^1$H NMR spectrum of pH-responsive precursor tBAM in Embodiment 1.
Figure 2:
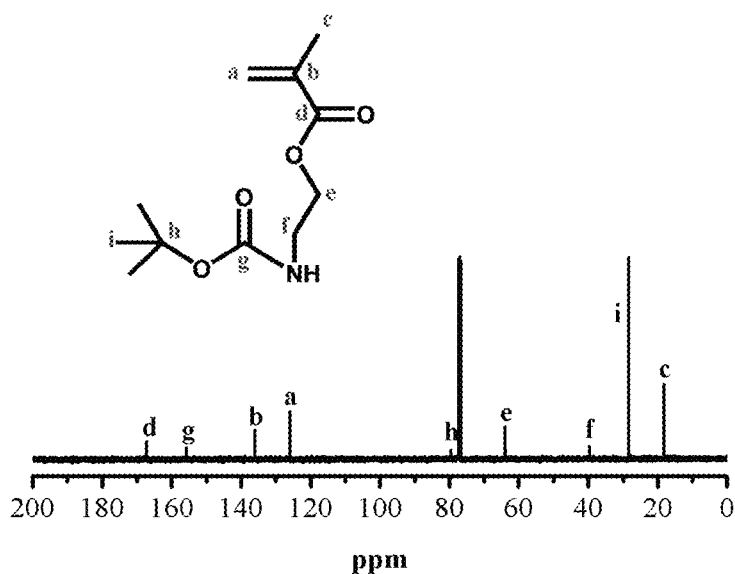
FIG. 2 is the $^{13}$C NMR spectrum of pH-responsive precursor tBAM in Embodiment 1.

The reaction formula is shown in formula (1). The structure and composition of the monomer were analyzed using $^1$H NMR and $^{13}$C NMR, and the results are shown in FIGS. 1 and 2.

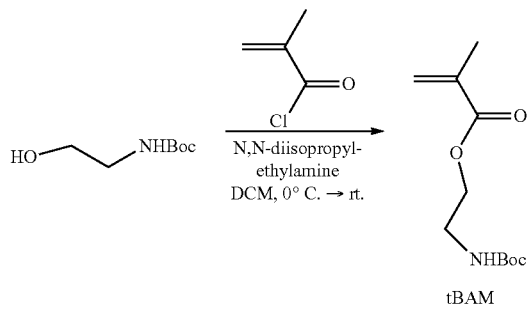

formula (1)

Embodiment 2: Precursor pH-Responsive Monomer (tBAM)

A 250 mL Schlenk flask was dried by a spirit lamp for 10 min. After cooling down, a magnetic stirring bar and tert-butyl N-(2-hydroxyethyl)carbamate (5 g, 31 mmol) were added to the flask, which was sealed by a rubber stopper. The flask was evacuated to vacuum and flushed with argon for three times. Then under Ar atmosphere, 100 mL dichloromethane (DCM) and N,N-diisopropylethylamine (5.4 mL, 31 mmol) were added in sequence. Methacryloyl chloride (9.9 mL, 93 mmol) was further added dropwise under ice bath condition. The reaction was carried out at 0° C. for 0.5 h and then at room temperature for another 48 h. The mixture was extracted successively with water, 400 mL 10% citric acid, 400 mL saturated NaHCO$_3$ and 400 mL saturated NaCl. The organic phase was collected and dried through Na$_2$SO$_4$ followed by rotary evaporation to remove part of the solvent. The obtained white liquid was precipitated by n-hexane, filtered, and finally dried under vacuum (40° C., 35 mb) for 24 h to obtain the product.

Embodiment 3: Preparation of an Amphipathic pH-Sensitive Star-Shaped Polymer β-CD-(PCL-b-PAEMA-b-PPEGMA)$_{21}$ (x:y:z=6:11:17)

(1) Preparation of a polycaprolactone polymer β-CD-(PCL-OH)$_{21}$: A 50 mL Schlenk flask was dried by a spirit lamp for 10 min. After cooling down, a magnetic stirring bar and β-CD (681 mg, 0.6 mmol) were added to the flask, which was sealed by a rubber stopper. The flask was evacuated to vacuum and flushed with argon for three times. Then under Ar atmosphere, the monomer ε-CL (8.0 mL, 75.6 mmol) and a required amount of Sn(Oct)$_2$ (0.1 wt. % of ε-CL, 86 mg) were added into the flask, after which three cycles of 'freeze-pump-heat' with liquid nitrogen were performed. Reaction was then carried out under oil bath at 110° C. for 24 h and argon protection. After the reaction, the crude polymer was dissolved in approximately 50 mL THF followed by adding to 300 mL water/methanol (1:1, v/v) mixture for precipitation. β-CD-(PCL-OH)$_{21}$ was collected and dried under vacuum (40° C., 35 mb).

Figure 3:
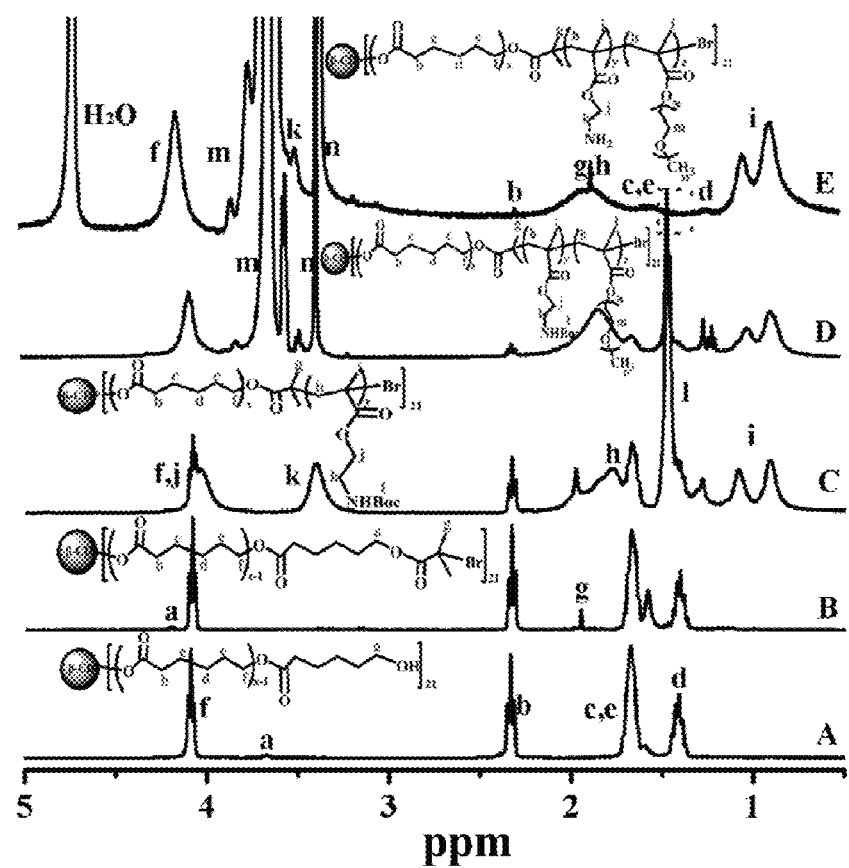
FIG. 3 shows the $^1$H NMR spectra of β-CD-(PCL-OH)$_{21}$ (A), macroinitiator β-CD-(PCL-Br)$_{21}$ (B), β-CD-(PCL-b-PtBAM)$_{21}$ (C), amphipathic star-shaped polymer β-CD-(PCL-b-PtBAM-b-PPEGMA)$_{21}$ (D), and amphipathic pH-sensitive star-shaped polymer β-CD-(PCL-b-PAEMA-b-PPEGMA)$_{21}$ (E) in Embodiment 3.
Figure 4:
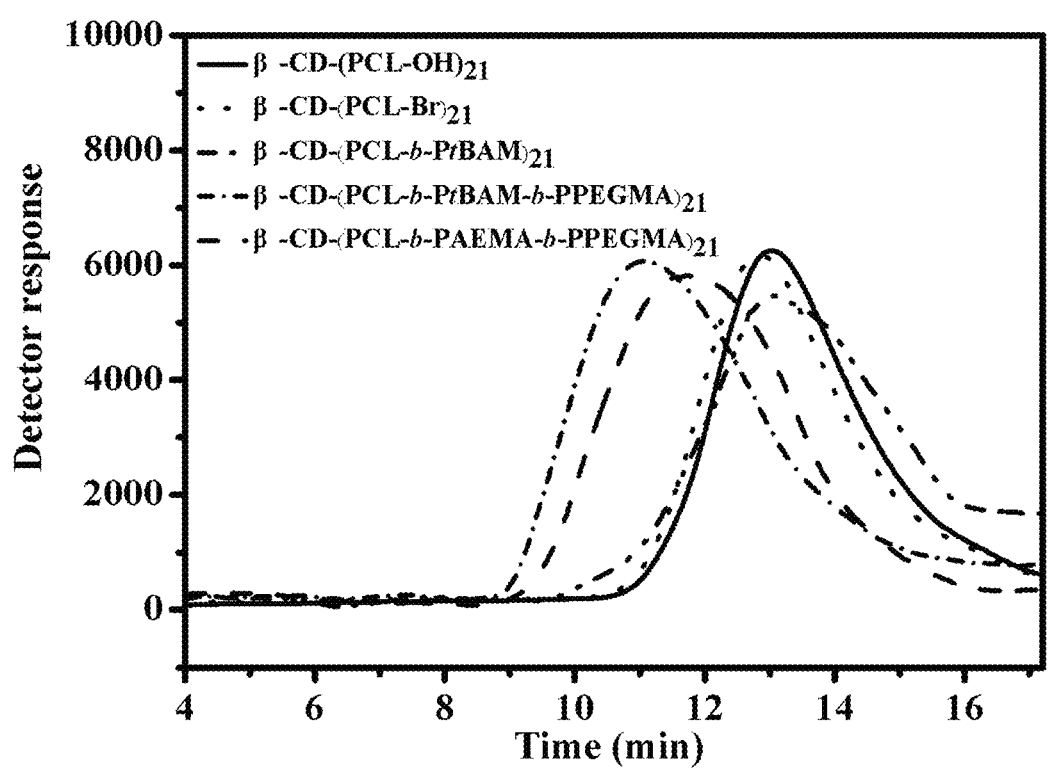
FIG. 4 shows the GPC traces of β-CD-(PCL-OH)$_{21}$ (A), macroinitiator β-CD-(PCL-Br)$_{21}$ (B), β-CD-(PCL-b-PtBAM)$_{21}$ (C), amphipathic star-shaped polymer β-CD-(PCL-b-PtBAM-b-PPEGMA)$_{21}$ (D), and amphipathic pH-sensitive star-shaped polymer β-CD-(PCL-b-PAEMA-b-PPEGMA)$_{21}$ (E) in Embodiment 3.
Figure 5:
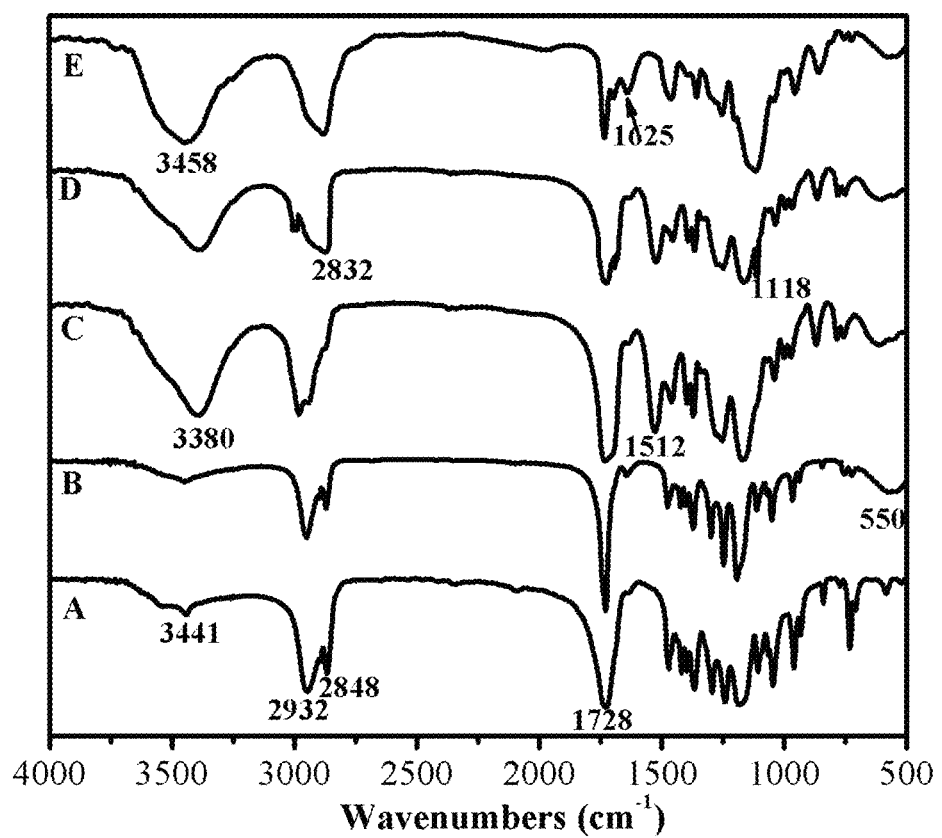
FIG. 5 shows the FT-IR spectra of β-CD-(PCL-OH)$_{21}$ (A), macroinitiator β-CD-(PCL-Br)$_{21}$ (B), β-CD-(PCL-b-PtBAM)$_{21}$ (C), amphipathic star-shaped polymer β-CD-(PCL-b-PtBAM-b-PPEGMA)$_{21}$ (D), and amphipathic pH-sensitive star-shaped polymer β-CD-(PCL-b-PAEMA-b-PPEGMA)$_{21}$ (E) in Embodiment 3.

The reaction formula is shown in formula (2). The structure and composition of β-CD-(PCL-OH)$_{21}$ were analyzed using $^1$H NMR, GPC and IR, and the results are shown in FIG. 3-5 ($M_n$=15499, $M_w/M_n$=2.75).

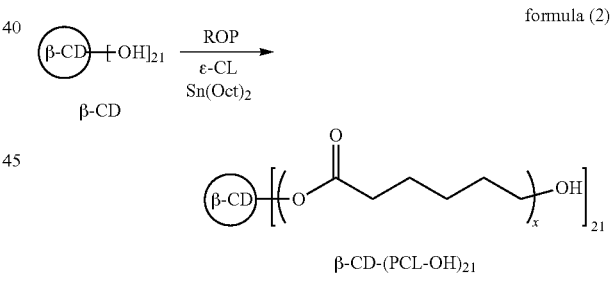

formula (2)

(2) Preparation of macroinitiator β-CD-(PCL-Br)$_{21}$: A magnetic stirring bar, β-CD-(PCL-OH)$_{21}$ (4650 mg, 0.3 mmol) and anhydrous THF (150 mL) were added to a dried 250 mL three-necked flask, and the flask was flushed with argon for 10 min. Then TEA (2.78 mL, 20 mmol) was injected into the flask after sealing the flask. After the solution was cooled to 0° C. with an ice/water bath, 2-bromoisobutyryl bromide (2.48 mL, 20 mmol) was added dropwise by an injector. The reaction was continued at 0° C. for 5 h and then at room temperature for another 24 h. After reaction, the mixture was passed through a neutral alumina column to remove quaternary ammonium salt. Most of the solvent was removed by rotary evaporation and water/methanol (1:1, v/v) mixture was added to precipitate the product twice, which was then filtered and dried under vacuum.

The reaction formula is shown in formula (3). The structure and composition were analyzed using $^1$H NMR, GPC and FT IR, and the results are shown in FIG. 3-5 ($M_n$=18628, $M_w/M_n$=1.79).

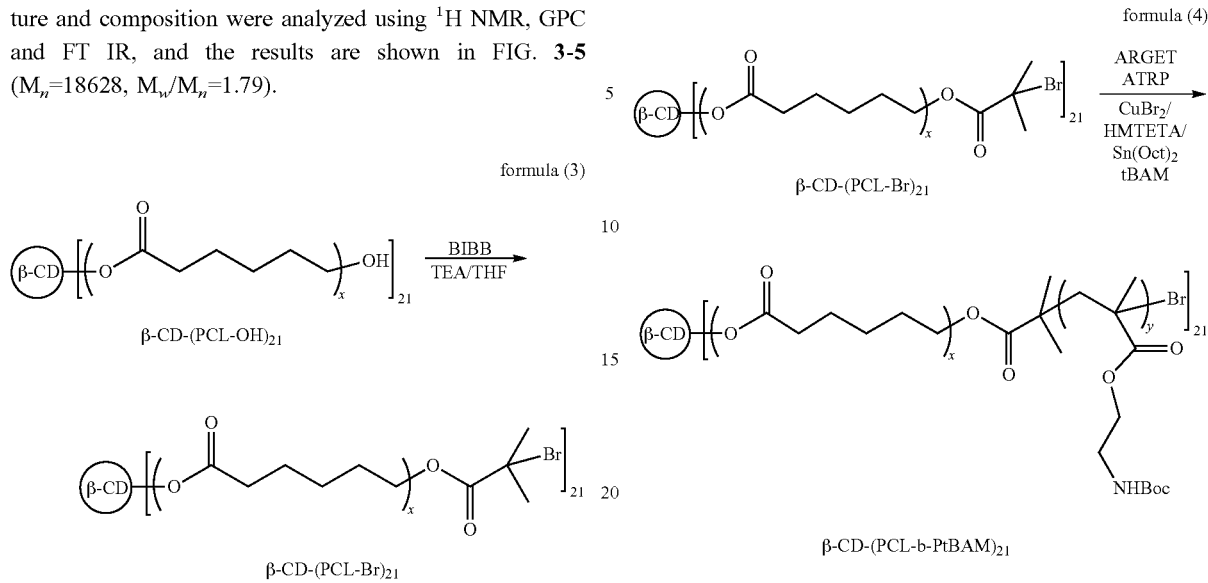

formula (3)

β-CD-(PCL-OH)$_{21}$

β-CD-(PCL-Br)$_{21}$ formula (4)

β-CD-(PCL-Br)$_{21}$

β-CD-(PCL-b-PtBAM)$_{21}$ (3) Preparation of pH-responsive polymer precursor β-CD-(PCL-b-PtBAM)$_{21}$: a magnetic stirring bar, macroinitiator β-CD-(PCL-Br)$_{21}$ (560 mg, 0.03 mmol) and CuBr$_2$ (10 mg, 0.045 mmol) were added to a dried 100 mL eggplant-shaped flask, which was sealed by rubber stopper. The flask was evacuated and flushed with argon for three times. Solvent (20 mL), tBAM (1905 mg, 6.93 mmol) and ligand HMTETA (62 μL, 0.24 mmol) were injected sequentially into the flask using syringes. The mixture was stirred for 10 min and Sn(Oct)$_2$ (78 μL, 0.24 mmol) dissolved in toluene (1 mL) was added into the flask. After stirring for 5 min, the mixture was heated under 80° C. oil bath for 24 h. The mixture was then cooled to room temperature, and THF (50 mL) was added into the flask followed by removal of catalyst through a neutral alumina column. The concentrated mixture was slowly added to 10-fold volume of n-hexane for precipitation. Finally the mixture was filtered and dried under vacuum (40° C., 35 mb) to obtain the product.

The reaction formula is shown in formula (4). The structure and composition were analyzed using $^1$H NMR, GPC and IR, and the results are shown in FIG. 3-5 ($M_n$=76840, $M_w/M_n$=1.88).

(4) Preparation of an amphipathic star-shaped polymer β-CD-(PCL-b-PtBAM-b-PPEGMA)$_{21}$: a magnetic stirring bar, macroinitiator β-CD-(PCL-b-PtBAM)$_{21}$ (2305 mg, 0.03 mmol) and CuBr$_2$ (10 mg, 0.045 mmol) were added to a dried 100 mL eggplant-shaped flask, which was sealed by rubber stopper. The flask was evacuated and flushed with argon for three times. Solvent (30 mL), monomer PEGMA (5985 mg, 10.71 mmol) and ligand HMTETA (62 μL, 0.24 mmol) were added sequentially into the flask using degassed syringes. The mixture was stirred for 10 min and Sn(Oct)$_2$ (78 μL, 0.24 mmol) dissolved in toluene (1 mL) was added into the flask. After stirring for 5 min, the mixture was heated under 80° C. oil bath for 72 h. The mixture was then cooled to room temperature, and THF (50 mL) was added into the flask followed by removal of catalyst through a neutral alumina column. The concentrated mixture was slowly added to 10-fold volume of n-hexane for precipitation. Finally the mixture was filtered and dried under vacuum (40° C., 35 mb) to obtain the amphipathic star-shaped polymer β-CD-(PCL-b-PtBAM-b-PPEGMA)$_{21}$.

The reaction formula is shown in formula (5). The structure and composition were analyzed using $^1$H NMR, GPC and IR, and the results are shown in FIG. 3-5 (246415, $M_w/M_n$=2.42).

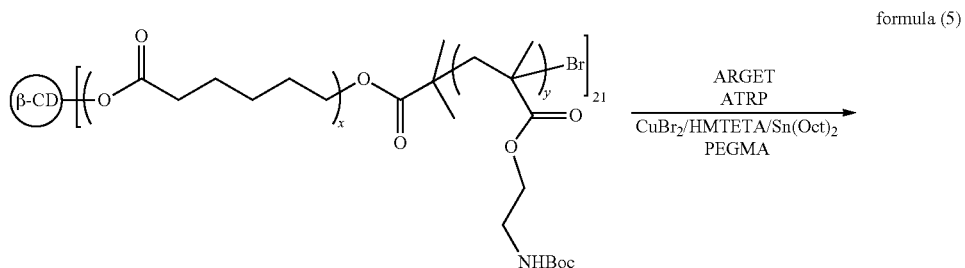

formula (5)

β-CD-(PCL-b-PtBAM)$_{21}$

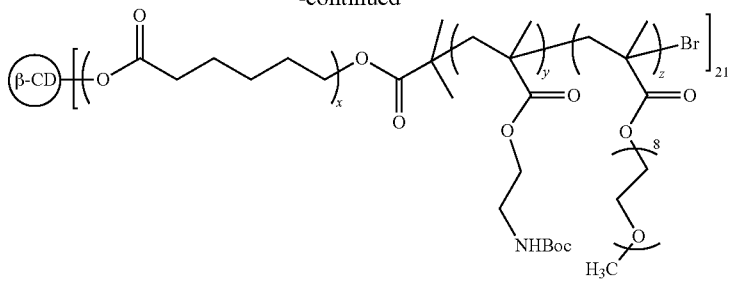

β-CD-(PCL-b-PtBAM-b-PPEGMA)$_{21}$ (5) Preparation of amphipathic pH-responsive β-cyclodextrin-based star-shaped polymer β-CD-(PCL-b-PAEMA-b-PPEGMA)$_{21}$: β-CD-(PCL-b-PtBAM-b-PPEGMA)$_{21}$ (1232 mg, 0.005 mmol) was dissolved in 20 mL DCM in a 100 mL round bottom flask. After cooling to 0° C. with ice/water bath, TFA (15 mL, 0.20 mmol) was slowly injected with vigorous stirring. The mixture was stirred at 0° C. for 2 h and then at room temperature for 6 h to remove tert-butyl ester. After removing all the solvent by rotary evaporation, THF (10 mL) was added into the flask and then the oil phase was precipitated by 200 mL n-hexane followed by drying overnight. Afterwards, the obtained polymer was washed with 0.5 M NaOH solution until pH=8.0, and immediately placed into a dialysis bag for three days. The final polymer was obtained by lyophilization (yield 98%).

The reaction formula is shown in formula (6). The structure and composition were analyzed using $^1$H NMR, GPC and IR, and the results are shown in FIG. 3-5 ($M_n$=218002, $M_w/M_n$=1.94).

Embodiment 4: Amphipathic pH-Sensitive Star-Shaped Polymer β-CD-(PCL-b-PAEMA-b-PPEGMA)$_{21}$ (x:y:z=4:20:30)

(1) Preparation of a polycaprolactone polymer β-CD-(PCL-OH)$_{21}$: A 50 mL Schlenk flask was dried by a spirit lamp for 10 min. After cooling down, a magnetic stirring bar and β-CD (681 mg, 0.6 mmol) were added to the flask, which was sealed by a rubber stopper. The flask was evacuated to vacuum and flushed with argon for three times. Then under Ar atmosphere, the monomer ε-CL (5.4 mL, 50.4 mmol) and a required amount of Sn(Oct)$_2$ (0.1 wt. % of ε-CL, 86 mg) were added into the flask, after which three cycles of 'freeze-pump-heat' with liquid nitrogen were performed. Reaction was then carried out under oil bath at 90° C. for 48 h and argon protection. After the reaction, the crude polymer was dissolved in approximately 50 mL THF followed by adding to 300 mL water/methanol (1:1, v/v) mixture for precipitation. β-CD-(PCL-OH)$_{21}$ was collected and dried under vacuum (40° C., 35 mb). The reaction formula is shown in formula (2). $M_n$=9576, $M_w/M_n$=1.86.

formula (6)

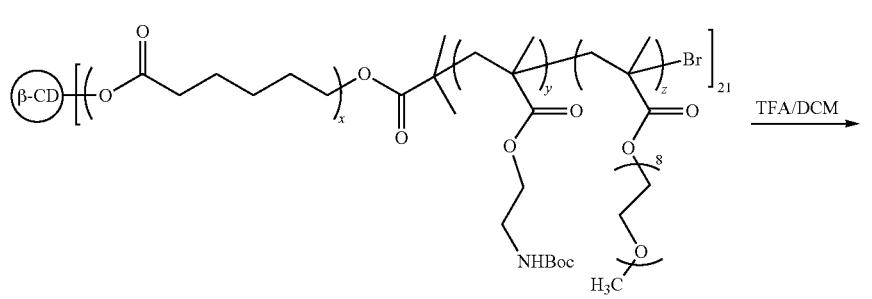

β-CD-(PCL-b-PAEMA-b-PPEGMA)$_{21}$ (2) Preparation of macroinitiator β-CD-(PCL-Br)$_{21}$: A magnetic stirring bar, β-CD-(PCL-OH)$_{21}$ (2872 mg, 0.3 mmol) and anhydrous THF (150 mL) were added to a dried 250 mL three-necked flask, and the flask was flushed with argon for 10 min. Then TEA (0.93 mL, 6.67 mmol) was injected into the flask after sealing the flask. After the solution was cooled to 0° C. with an ice/water bath, 2-bromoisobutyryl bromide (0.83 mL, 6.67 mmol) was added dropwise by an injector. The reaction was continued at 0° C. for 6 h and then at room temperature for another 24 h. After reaction, the mixture was passed through a neutral alumina column to remove quaternary ammonium salt. Most of the solvent was removed by rotary evaporation and water/methanol (1:1, v/v) mixture was added to precipitate the product twice, which was then filtered and dried under vacuum. $M_n$=10711, $M_w/M_n$=1.93

(3) Preparation of pH-responsive polymer precursor β-CD-(PCL-b-PtBAM)$_{21}$: a magnetic stirring bar, macroinitiator β-CD-(PCL-Br)$_{21}$ (322 mg, 0.03 mmol) and CuBr$_2$ (10 mg, 0.045 mmol) were added to a dried 100 mL eggplant-shaped flask, which was sealed by rubber stopper. The flask was evacuated and flushed with argon for three times. Solvent (20 mL), tBAM (3463 mg, 12.6 mmol) and ligand HMTETA (78 μL, 0.3 mmol) were injected sequentially into the flask using syringes. The mixture was stirred for 10 min and Sn(Oct)$_2$ (97.5 μL, 0.3 mmol) dissolved in toluene (1 mL) was added into the flask. After stirring for 5 min, the mixture was heated under 60° C. oil bath for 48 h. The mixture was then cooled to room temperature, and THF (50 mL) was added into the flask followed by removal of catalyst through a neutral alumina column. The concentrated mixture was slowly added to 10-fold volume of n-hexane for precipitation. Finally the mixture was filtered and dried under vacuum (45° C., 35 mb) to obtain the product. $M_n$=116551, $M_w/M_n$=1.69

(4) Preparation of an amphipathic star-shaped polymer β-CD-(PCL-b-PtBAM-b-PPEGMA)$_{21}$: a magnetic stirring bar, macroinitiator β-CD-(PCL-b-PtBAM)$_{21}$ (3495 mg, 0.03 mmol) and CuBr$_2$ (10 mg, 0.045 mmol) were added to a dried 100 mL eggplant-shaped flask, which was sealed by rubber stopper. The flask was evacuated and flushed with argon for three times. Solvent (30 mL), monomer PEGMA (10561 mg, 10.71 mmol) and ligand HMTETA (78 μL, 0.3 mmol) were added sequentially into the flask using degassed syringes. The mixture was stirred for 10 min and Sn(Oct)$_2$ (97.5 μL, 0.3 mmol) dissolved in toluene (1 mL) was added into the flask. After stirring for 5 min, the mixture was heated under 90° C. oil bath for 48 h. The mixture was then cooled to room temperature, and THF (50 mL) was added into the flask followed by removal of catalyst through a neutral alumina column. The concentrated mixture was slowly added to 10-fold volume of n-hexane for precipitation. Finally the mixture was filtered and dried under vacuum (45° C., 35 mb) to obtain the amphipathic star-shaped polymer β-CD-(PCL-b-PtBAM-b-PPEGMA)$_{21}$. $M_n$=415801, $M_w/M_n$=2.21

(5) Preparation of amphipathic pH-responsive β-cyclodextrin-based star-shaped polymer β-CD-(PCL-b-PAEMA-b-PPEGMA)$_{21}$: β-CD-(PCL-b-PtBAM-b-PPEGMA)$_{21}$ (2079 mg, 0.005 mmol) was dissolved in 20 mL DCM in a 100 mL round bottom flask. After cooling to 0° C. with ice/water bath, TFA (22.5 mL, 0.30 mmol) was slowly injected with vigorous stirring. The mixture was stirred at 0° C. for 2 h and then at room temperature for 10 h to remove tert-butyl ester. After removing all the solvent by rotary evaporation, THF (10 mL) was added into the flask and then the oil phase was precipitated by 200 mL n-hexane followed by drying overnight. Afterwards, the obtained polymer was washed with 0.5 M NaOH solution until pH=8.0, and immediately placed into a dialysis bag for three days. The final polymer was obtained by lyophilization (yield 98%). $M_n$=364141, $M_w/M_n$=1.77

Embodiment 5: Amphipathic pH-Sensitive Star-Shaped Polymer β-CD-(PCL-b-PAEMA-b-PPEGMA)$_{21}$ (x:y:z=15:3:10)

(1) Preparation of a polycaprolactone polymer β-CD-(PCL-OH)$_{21}$: A 50 mL Schlenk flask was dried by a spirit lamp for 10 min. After cooling down, a magnetic stirring bar and β-CD (681 mg, 0.6 mmol) were added to the flask, which was sealed by a rubber stopper. The flask was evacuated to vacuum and flushed with argon for three times. Then under Ar atmosphere, the monomer ε-CL (20.25 mL, 189 mmol) and a required amount of Sn(Oct)$_2$ (0.1 wt. % of ε-CL, 86 mg) were added into the flask, after which three cycles of 'freeze-pump-heat' with liquid nitrogen were performed. Reaction was then carried out under oil bath at 130° C. for 24 h and argon protection. After the reaction, the crude polymer was dissolved in approximately 50 mL THF followed by adding to 300 mL water/methanol (1:1, v/v) mixture for precipitation. β-CD-(PCL-OH)$_{21}$ was collected and dried under vacuum (45° C., 35 mb). The reaction formula is shown in formula (2). $M_n$=35910, $M_w/M_n$=2.16.

(2) Preparation of macroinitiator β-CD-(PCL-Br)$_{21}$: A magnetic stirring bar, β-CD-(PCL-OH)$_{21}$ (10773 mg, 0.3 mmol) and anhydrous THF (150 mL) were added to a dried 250 mL three-necked flask, and the flask was flushed with argon for 10 min. Then TEA (3.72 mL, 27 mmol) was injected into the flask after sealing the flask. After the solution was cooled to 0° C. with an ice/water bath, 2-bromoisobutyryl bromide (3.32 mL, 27 mmol) was added dropwise by an injector. The reaction was continued at 0° C. for 4 h and then at room temperature for another 48 h. After reaction, the mixture was passed through a neutral alumina column to remove quaternary ammonium salt. Most of the solvent was removed by rotary evaporation and water/methanol (1:1, v/v) mixture was added to precipitate the product twice, which was then filtered and dried under vacuum. $M_n$=37045, $M_w/M_n$=1.76

(3) Preparation of pH-responsive polymer precursor β-CD-(PCL-b-PtBAM)$_{21}$: a magnetic stirring bar, macroinitiator β-CD-(PCL-Br)$_{21}$ (1112 mg, 0.03 mmol) and CuBr$_2$ (10 mg, 0.045 mmol) were added to a dried 100 mL eggplant-shaped flask, which was sealed by rubber stopper. The flask was evacuated and flushed with argon for three times. Solvent (20 mL), tBAM (520 mg, 1.89 mmol) and ligand HMTETA (93 μL, 0.36 mmol) were injected sequentially into the flask using syringes. The mixture was stirred for 10 min and Sn(Oct)$_2$ (117 μL, 0.36 mmol) dissolved in toluene (1 mL) was added into the flask. After stirring for 5 min, the mixture was heated under 80° C. oil bath for 24 h. The mixture was then cooled to room temperature, and THF (50 mL) was added into the flask followed by removal of catalyst through a neutral alumina column. The concentrated mixture was slowly added to 10-fold volume of n-hexane for precipitation. Finally the mixture was filtered and dried under vacuum (45° C., 35 mb) to obtain the product. $M_n$=52921, $M_w/M_n$=1.88

(4) Preparation of an amphipathic star-shaped polymer β-CD-(PCL-b-PtBAM-b-PPEGMA)$_{21}$: a magnetic stirring bar, macroinitiator β-CD-(PCL-b-PtBAM)$_{21}$ (1588 mg, 0.03 mmol) and CuBr$_2$ (10 mg, 0.045 mmol) were added to a dried 100 mL eggplant-shaped flask, which was sealed by rubber stopper. The flask was evacuated and flushed with argon for three times. Solvent (30 mL), monomer PEGMA (3520 mg, 6.3 mmol) and ligand HMTETA (93 μL, 0.36 mmol) were added sequentially into the flask using degassed syringes. The mixture was stirred for 10 min and Sn(Oct)$_2$ (117 μL, 0.36 mmol) dissolved in toluene (1 mL) was added into the flask. After stirring for 5 min, the mixture was heated under 60° C. oil bath for 96 h. The mixture was then cooled to room temperature, and THF (50 mL) was added into the flask followed by removal of catalyst through a neutral alumina column. The concentrated mixture was slowly added to 10-fold volume of n-hexane for precipitation. Finally the mixture was filtered and dried under vacuum (45° C., 35 mb) to obtain the amphipathic star-shaped polymer β-CD-(PCL-b-PtBAM-b-PPEGMA)$_{21}$. $M_n$=152641, $M_w/M_n$=2.03

(5) Preparation of amphipathic pH-responsive β-cyclodextrin-based star-shaped polymer β-CD-(PCL-b-PAEMA-b-PPEGMA)$_{21}$: β-CD-(PCL-b-PtBAM-b-PPEGMA)$_{21}$ (764 mg, 0.005 mmol) was dissolved in 20 mL DCM in a round bottom flask. After cooling to 0° C. with ice/water bath, TFA (7.5 mL, 0.10 mmol) was slowly injected with vigorous stirring. The mixture was stirred at 0° C. for 4 h and then at room temperature for 4 h to remove tert-butyl ester. After removing all the solvent by rotary evaporation, THF (10 mL) was added into the flask and then the oil phase was precipitated by 200 mL n-hexane followed by drying overnight. Afterwards, the obtained polymer was washed with 0.5 M NaOH solution until pH=8.0, and immediately placed into a dialysis bag for three days. The final polymer was obtained by lyophilization (yield 98%). $M_n$=144922, $M_w/M_n$=1.92

Embodiment 6: Preparation of Amphipathic pH-Responsive Star-Shaped Polymers Unimolecular Micelles Unimolecular micelles were prepared by dialysis. Briefly, amphipathic the pH-sensitive star-shaped polymer β-CD-(PCL-b-PAEMA-b-PPEGMA)$_{21}$ (100 mg) obtained in embodiment 3 was dissolved in DMSO (40 mL) and stirred for 4 h. The solution was then dialyzed against water for 24 h using a dialysis bag, wherein the fresh deionized water was replaced every 2 h during the first 12 h and then every 6 h during the following 12 h. After dialysis, the dialyzed solution were filtered by a membrane filter (0.45 μm pore) and lyophilized to obtain white powdery blank unimolecular micelles.

Figure 6:
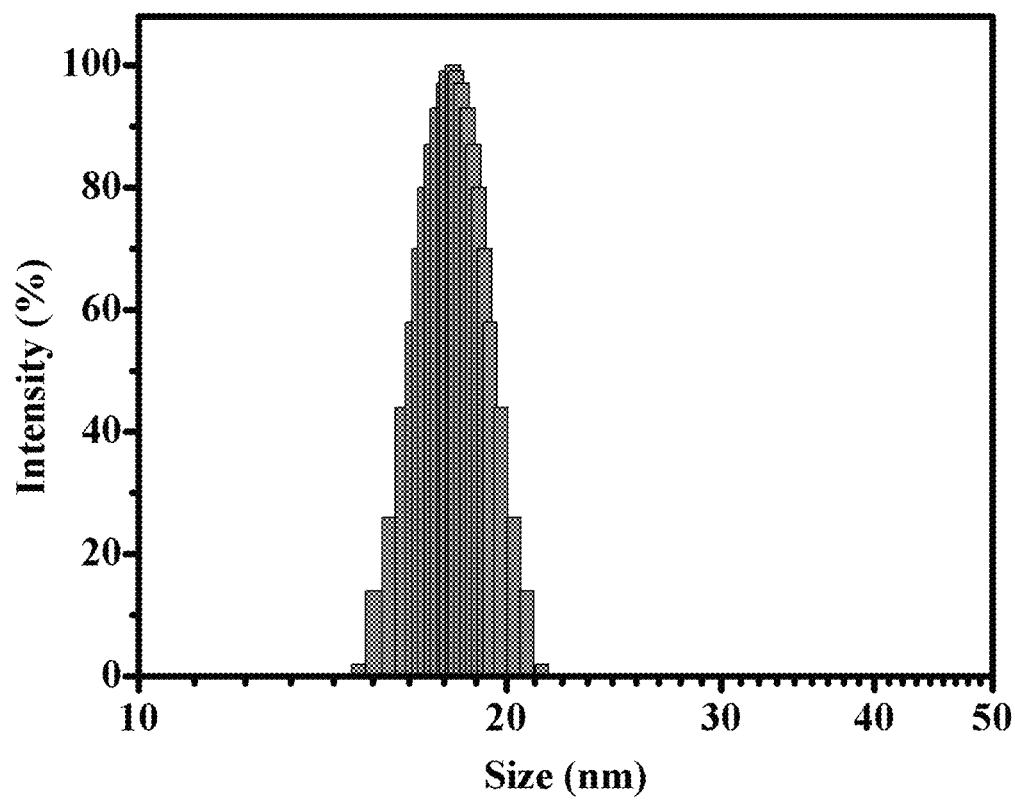
FIG. 6 shows the DLS plot of β-CD-(PCL-b-PAEMA-b-PPEGMA)$_{21}$ unimolecular micelles in Embodiment 6.
Figure 7:
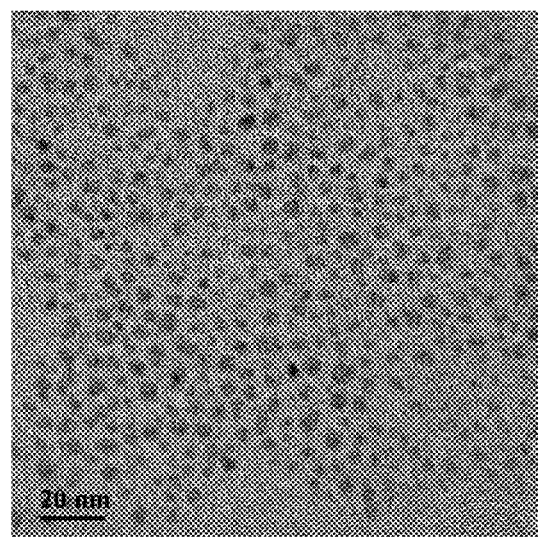
FIG. 7 shows the TEM image of β-CD-(PCL-b-PAEMA-b-PPEGMA)$_{21}$ unimolecular micelles in Embodiment 6.

Particle size (Dh), distribution (PDI), and zeta potential of the blank unimolecular micelles were measured by dynamic light scattering (DLS). The particle size is 18 nm (FIG. 6), PDI is 0.41 and zeta potential is 15.6 mV. The particle size determined by TEM image was around 10.5 nm (FIG. 7).

Embodiment 7: Preparation of Unimolecular Micelle-Stabilized AuNPs

Figure 8:
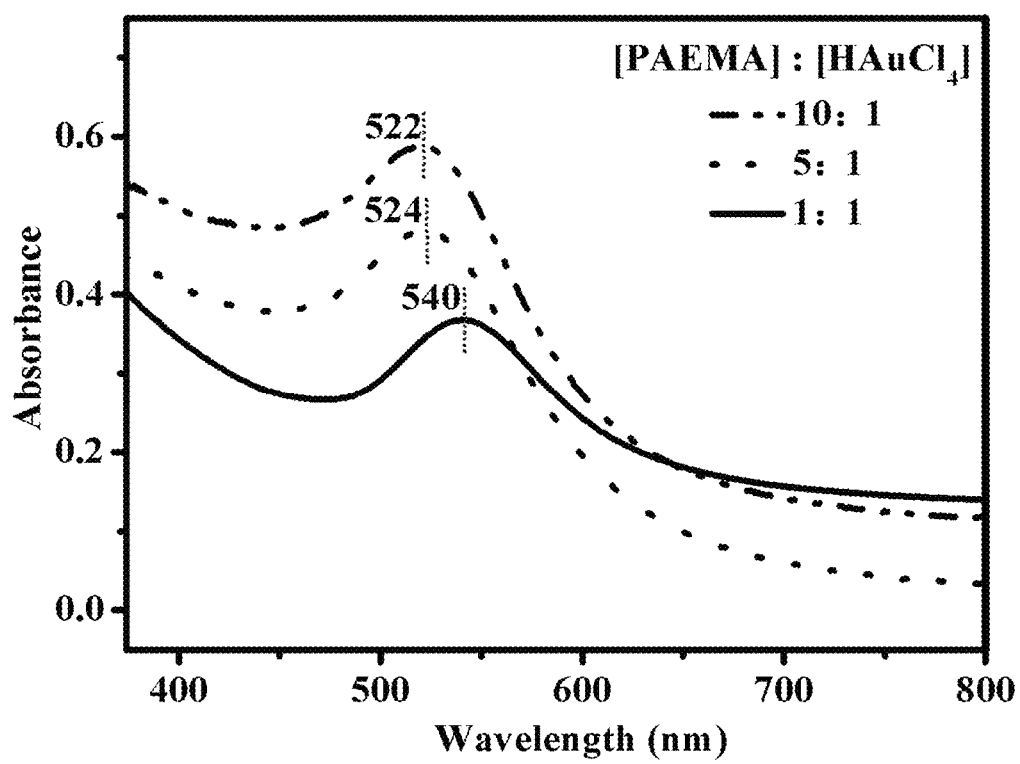
FIG. 8 is the UV-vis absorption spectra of β-CD-(PCL-b-PAEMA-b-PPEGMA)$_{21}$/Au with different molar ratios of [AEMA]:[HAuCl$_4$] in Embodiment 7.
Figure 9:
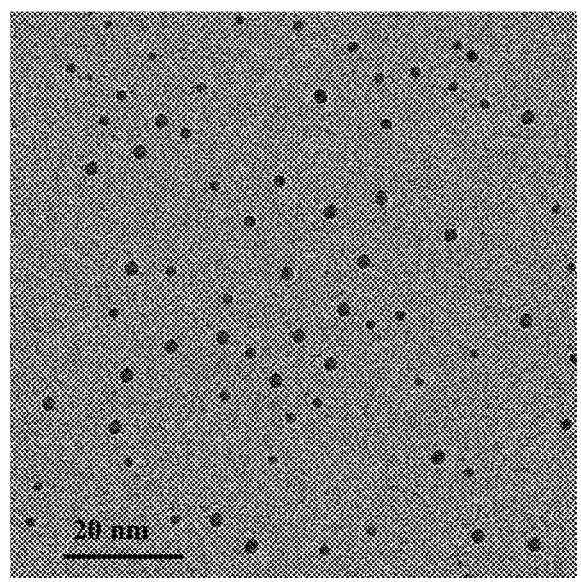
FIG. 9 shows the TEM image of β-CD-(PCL-b-PAEMA-b-PPEGMA)$_{21}$/Au in Embodiment 7.
Figure 10:
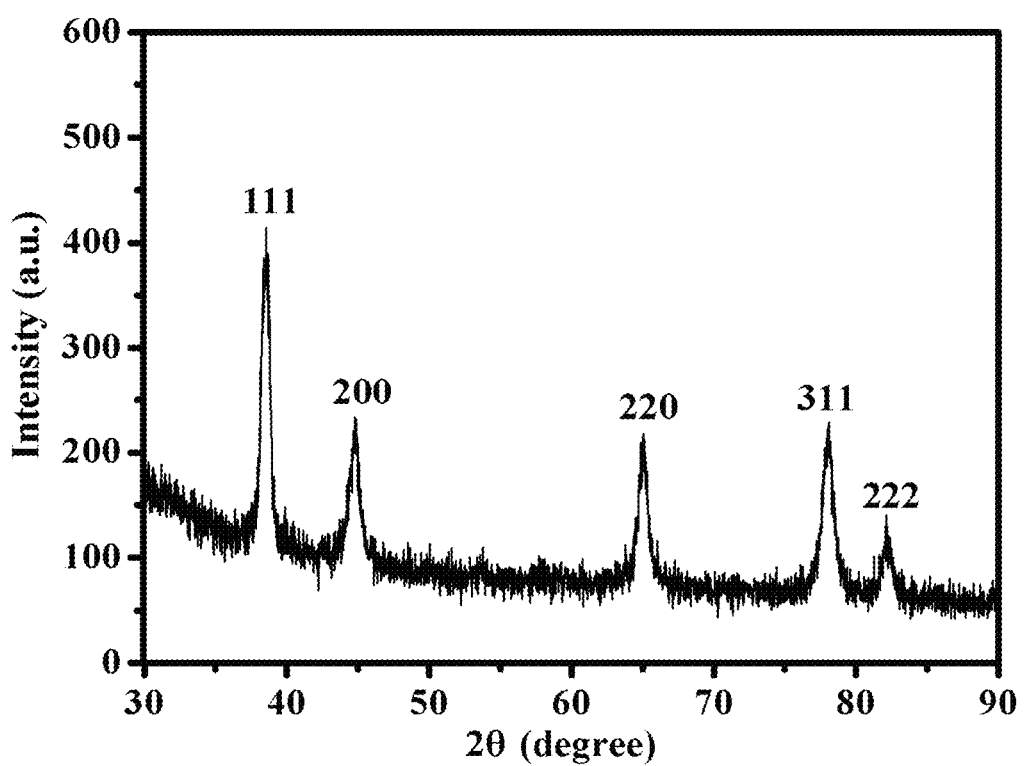
FIG. 10 shows the XRD plot of β-CD-(PCL-b-PAEMA-b-PPEGMA)$_{21}$/Au in Embodiment 7.

Briefly, β-CD-(PCL-b-PAEMA-b-PPEGMA)$_{21}$ obtained in embodiment 5 (100 mg, [PAEMA]=2.4 mM) and 20 mL deionized water were added to a 50 mL beaker with stirring to dissolve for 2 h. HAuCl$_4$ (24 mM, [DMAEMA]:[HAuCl$_4$]=1/5/10) solution was further added dropwise to the polymer solution with stirring to mix together. Then NaBH$_4$ ([NaBH$_4$]: [HAuCl$_4$]=3:1) was added dropwise to the mixture solution, after which the reaction was carried out at room temperature in darkness for 48 h to obtain gold-nanoparticle-loaded composite material β-CD-(PCL-b-PAEMA-b-PPEGMA)$_{21}$/Au. With increasing concentrations of HAuCl$_4$, the maximum wavelength ($\lambda_{max}$) of AuNPs shown in UV-vis spectra were 522 nm, 524 nm, and 540 nm, which were induced by the plasma resonance excitation or interband transition of gold nanoparticle and were characteristic surface plasma resonance absorption peak of spherical gold nanoparticle (FIG. 8). The AuNP size under TEM was 3.5 nm when [AEMA]:[HAuCl$_4$]=5 (FIG. 9). X-ray diffraction spectrum in FIG. 10 shows peaks at 38.5°, 44.8°, 64.2° and 78.0° corresponding to (111), (200), (220) and (311) crystal faces of standard gold diffraction spectrum, respectively, which proves the face-centered-cubic (fcc) crystal structure of gold nanoparticle.

Embodiment 8: Preparation of Amphipathic pH-Responsive Star-Shaped Polymer Drug-Loaded Micelles The amphipathic pH-responsive star-shaped polymer drug-loaded micelles were prepared by dialysis. DOX•HCl (10~50 mg) was first mixed with 2 times molar equivalent of triethylamine in 20 mL DMSO followed by stirring overnight to obtain DOX base. 100 mg β-CD-(PCL-b-PAEMA-b-PPEGMA)$_{21}$/Au obtained in Embodiment 7 was mixed with another 20 mL DMSO and a micelle system was obtained after complete dissolvation. The micelle system was mixed with the DOX solution. After that, the mixture was stirred for 4 h and then dialyzed against deionized water using a dialysis bag, wherein the fresh deionized water was replaced every 2 h during the first 12 h and then every 6 h during the following 12 h. After dialysis, the dialyzed solution was filtered by a membrane filter (0.45 μm pore) and lyophilized to obtain red powdery DOX-loaded micelles.

Figure 11:
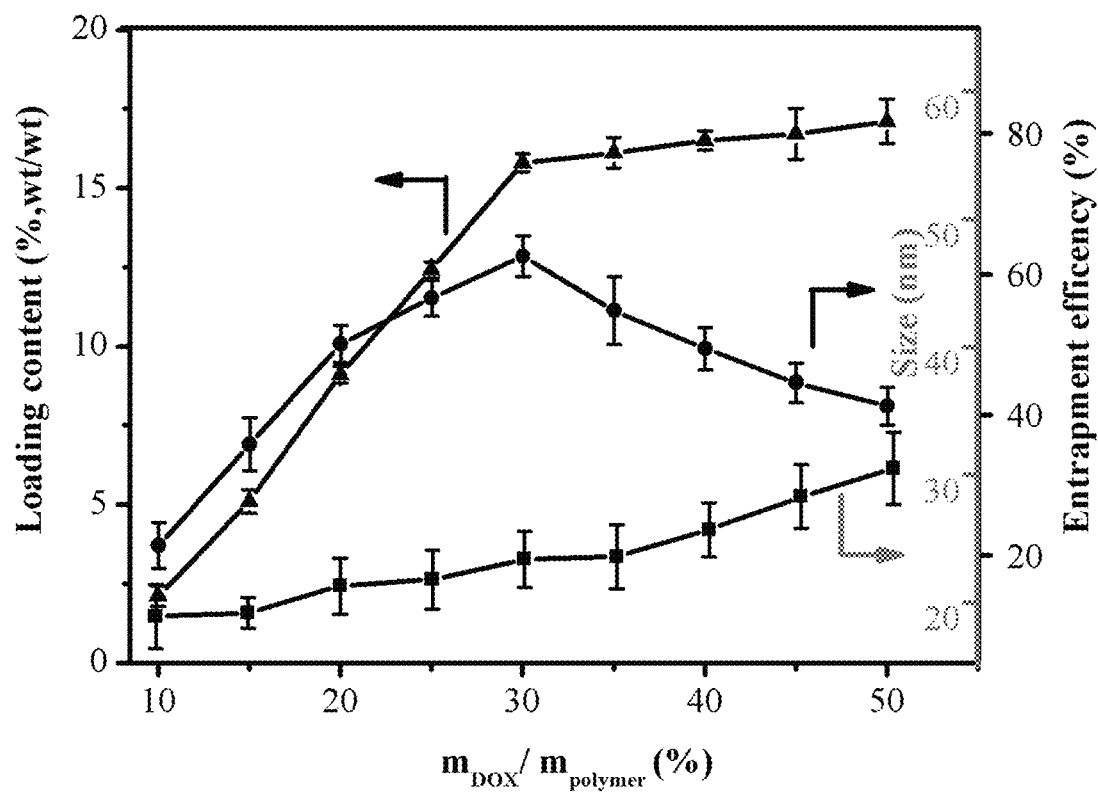
FIG. 11 shows the loading amount, entrapment efficiency, and particle size of β-CD-(PCL-b-PAEMA-b-PPEGMA)$_{21}$/Au/DOX in Embodiment 8.

The DOX-loaded micelles were examined by UV-vis spectrophotometer. The calculated LC was 2.1-17.1%, EE was 21.0-62.5% and particle size was 18.9-30.5 nm (FIG. 11).

Embodiment 9: In Vitro Release of Drug-Loaded Micelles

Figure 12:
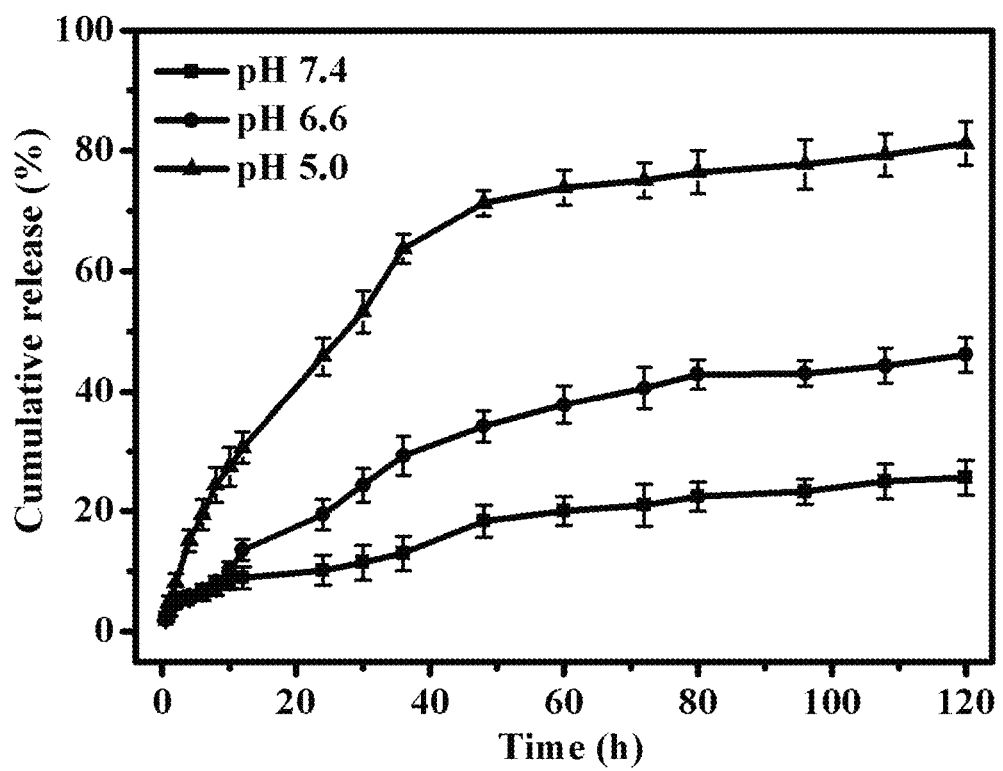
FIG. 12 illustrates the in vitro drug release profiles of β-CD-(PCL-b-PAEMA-b-PPEGMA)$_{21}$/Au/DOX in Embodiment 9.

The release profiles of DOX under different pH value were measured by dissolution Tester. 5 mg of DOX-loaded micelles obtained in Embodiment 8 were dispersed in 5 mL of PBS buffer whose pH=5.0, 6.5 and 7.4, respectively. Then the solutions were placed in dialysis bags. The whole bags were placed into 46 mL of PBS and then in dissolution tester with constant shaking (100 rpm) at 37° C. to promote in vitro release. At each predetermined time interval, a 3-mL sample was collected for UV analysis, meantime an equal volume of fresh buffer solution was added. The amounts of released DOX in the buffer solution at different time were measured by UV-vis spectrophotometer, as shown in FIG. 12.

DOX release rate increased obviously as pH decreased from 7.4 to 5.0. At pH 7.4, only 25% of DOX was released after 120 h owing to compact structure of micelles. In the slightly acidic extracellular space of the tumor cell (pH 6.6), approximately 46% of DOX was released at 120 h. In the more acidic (pH 5.0) environment of tumor cell, the release rate of DOX significantly increased, wherein approximately 45% and 81% of DOX was released after 24 h and 120 h, respectively.

Embodiment 10: Cytotoxicity Assay

100 μL DMEM mediums were added to the surrounding wells of a 96-well plate as control groups, and other wells were seeded with 100 μL HepG2 cell culture media (American Type Culture Collection ATCC, HB-8065™) with a concentration of $1\times10^4$ cells/well. The plate was placed at 37° C. and saturated humidity in a $CO_2$ (5%) incubator for 24 h. During this process, cells adhered to the bottom of 96-well plates and began to resume growth.

Subsequently, the blank micelles (product of embodiment 6), β-CD-(PCL-b-PAEMA-b-PPEGMA)$_{21}$/Au obtained in Embodiment 7, DOX-loaded micelles obtained in Embodiment 8, and free DOX were diluted by cell culture medium to different concentration gradients. After removing the cell culture medium from wells 2 to 11 in a 96-well plate, 100 μL of the above solutions were added separately as the experimental group. 100 μL of fresh cell culture medium was added to column 11 as control groups. Parallel experiments were done six times for each concentration.

After 48 h incubation, the supernatant from all wells with cells was aspirated, and the cells were rinsed with 200 μL PBS, which was aspirated subsequently. From column 2 to column 11, 20 μL of MTT solution and 180 μL of fresh medium were added to each well, and the 96-well plate was placed in an incubator for 4 h.

The unreduced MTT solution and medium were aspirated, each well was washed with 200 pt of PBS, which was aspirated subsequently. From column 2 to column 11, 200 μL DMSO was added to each well to dissolve the MTT crystals. The 96-well plate was shaken in a 37° C. shaker for 15 min, and then the absorbance of each well at 570 nm was measured using a microplate reader. The relative cell viability (%) was calculated using the equation as follows:

Cell viability(%)=(OD$_{test}$/OD$_{control}$)×100%.

Figure 13:
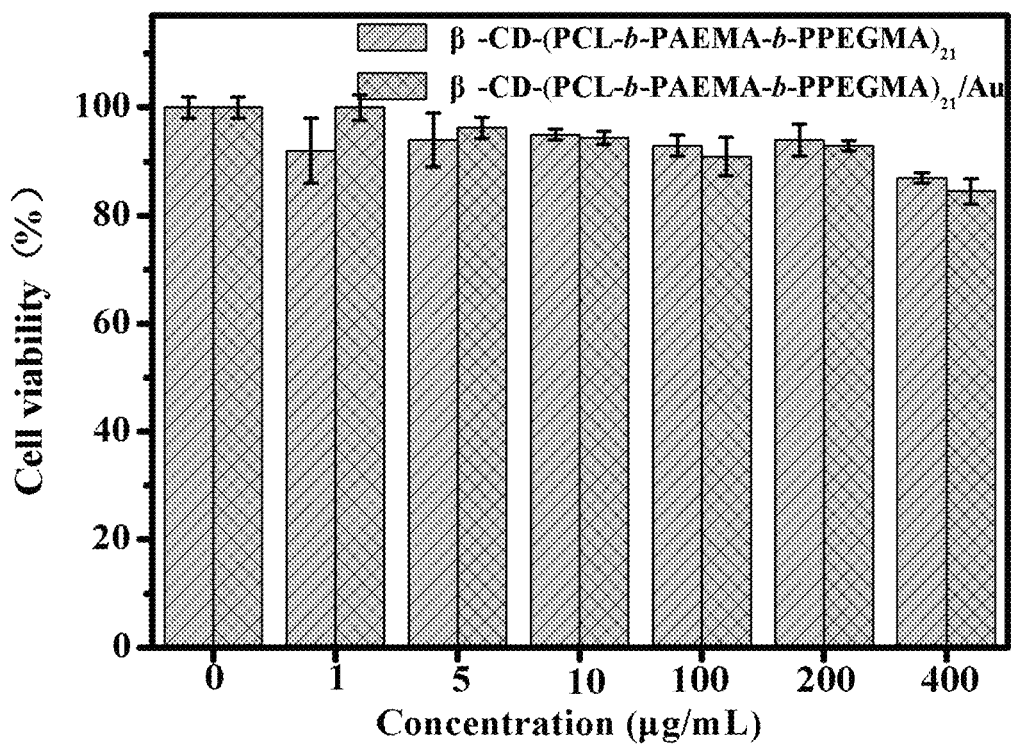
FIG. 13 illustrates the cytotoxicity of blank micelles and β-CD-(PCL-b-PAEMA-b-PPEGMA)$_{21}$/Au in Embodiment 10.

FIG. 13 shows the results of the cytotoxicity test of blank micelles (Embodiment 6) and β-CD-(PCL-b-PAEMA-b-PPEGMA)$_{21}$/Au (Embodiment 7). As the concentration increases from 0 to 400 μg/mL, blank micelles and β-CD-(PCL-b-PAEMA-b-PPEGMA)$_{21}$/Au still exhibit more than 80% cell viability, indicating that the polymer has low cytotoxicity.

Figure 14:
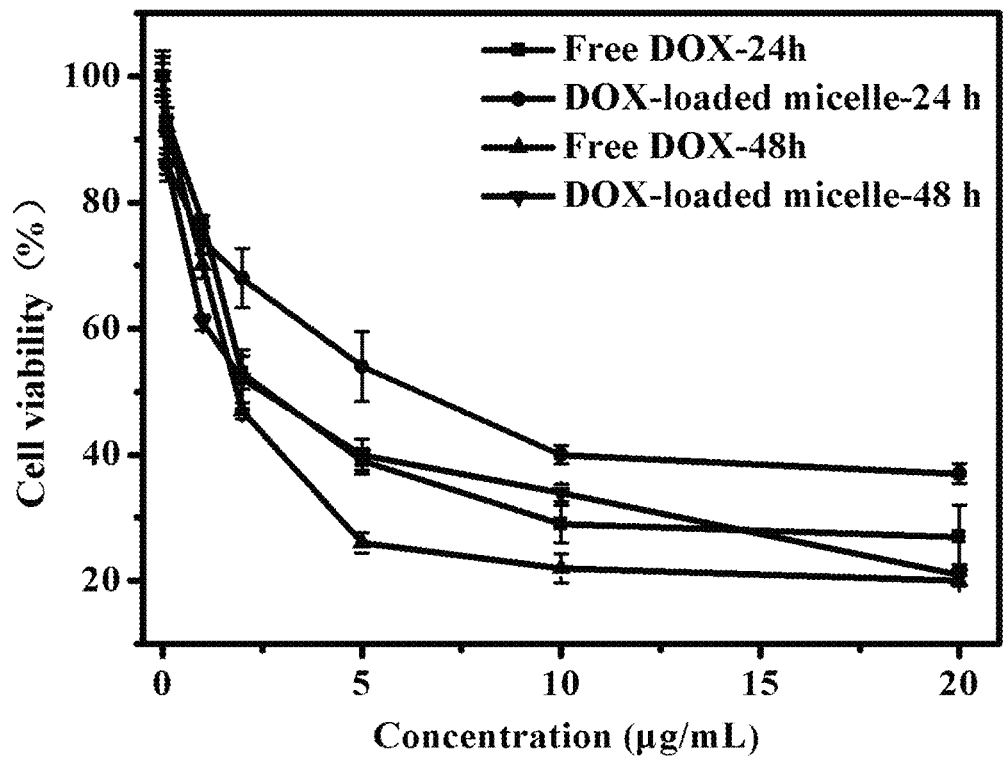
FIG. 14 illustrates the cytotoxicity of drug-loaded micelles in Embodiment 11.

FIG. 14 shows the results of the cytotoxicity test of DOX-loaded micelles in Embodiment 8. Low-dose (0.1 mg/L) DOX-loaded micelles had a lethal effect on cancer cells; DOX-loaded micelles and free doxorubicin were similar in cytotoxicity with more than 77% of the cell killed at high concentrations (20 mg/L), indicating that the loaded DOX still has good anti-cancer activity.

Embodiment 11: CT Imaging Test (1) In Vitro CT Imaging Test of the Material 29.88 mg of β-CD-(PCL-b-PAEMA-b-PPEGMA)$_{21}$/Au/DOX (product of Embodiment 8) was dissolved in 580 μL of PBS buffer to prepare a solution with 0.1M gold and then diluted to obtain solutions with different concentration of gold, the volume of which is 200 μL respectively. The solutions were then loaded into 1.5 mL centrifuge tubes. The same concentrations of Omnipaque solutions were used as a comparison. CT scanning was then performed to measure the CT signal of each picture.

(2) In Vitro CT Imaging Test of HepG2

Six-well plates were used to culture HepG2 cells with a certain amount of β-CD-(PCL-b-PAEMA-b-PPEGMA)$_{21}$/Au/DOX material (product of Embodiment 8) for CT scan at a density of $2\times10^6$ cells/well. After being cultured over night, the old medium was removed, then 2.35 mL of fresh medium and 250 μL of material were added, after which the plate was placed in the incubator and cultivated for 4 h. Finally, the remaining material was washed out with PBS, and the cells were collected and placed in 1.5-mL centrifuge tubes. After centrifugation at 1000 r/min for 5 min, the supernatant was discarded, the cells at the bottom were retained, and the solutions were homogenized with the addition of 0.2 mL of PBS. By comparing the X-ray absorption coefficients, the CT imaging effect of β-CD-(PCL-b-PAEMA-b-PPEGMA)$_{21}$/Au/DOX on HepG2 cells was analyzed using an in vitro CT scan.

Figure 15:
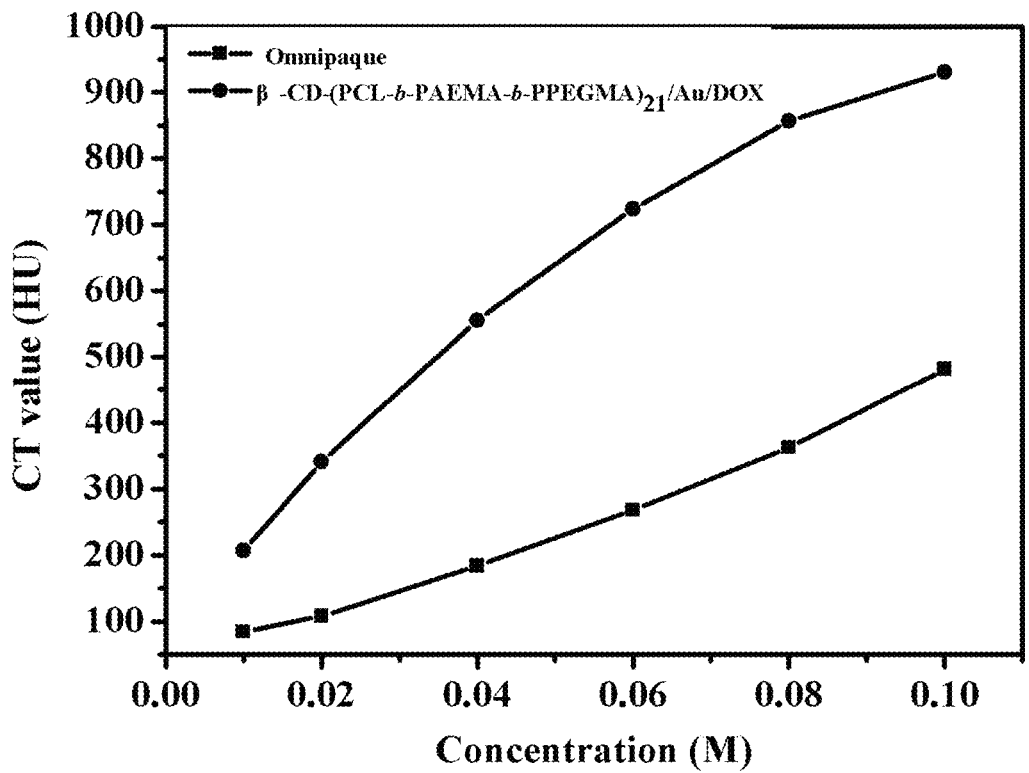
FIG. 15 shows the CT values of in vitro materials in Embodiment 11.
Figure 16:
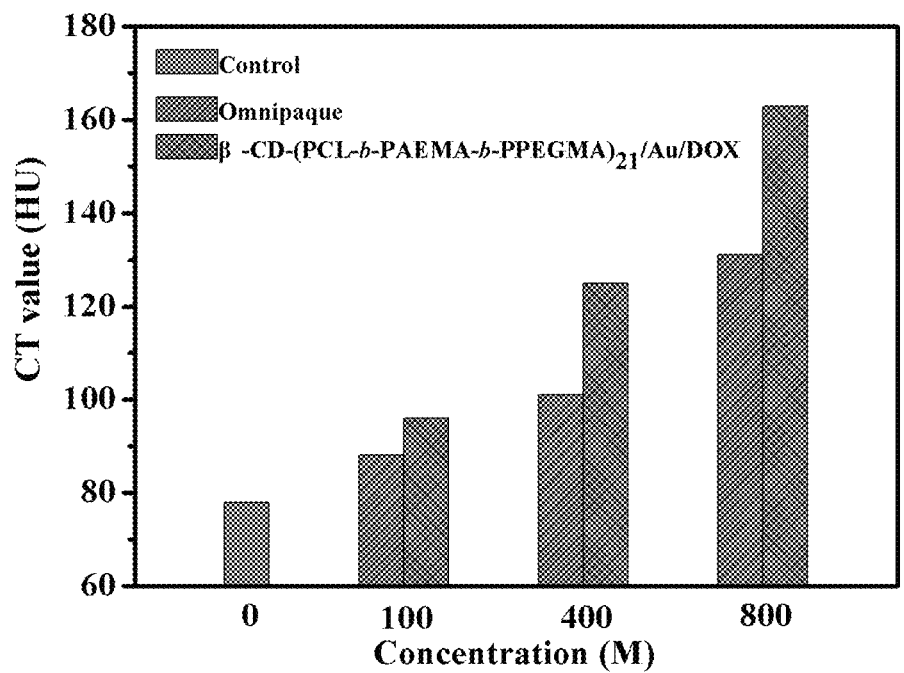
FIG. 16 shows the CT values of in vitro cells in Embodiment 11.

CT imaging results for the product of Embodiment 8 were shown in FIG. 15 (in vitro materials CT imaging) and FIG. 16 (in vitro cell CT imaging). With increasing concentrations, the HU values of β-CD-(PCL-b-PAEMA-b-PPEGMA)$_{21}$/Au/DOX and Omnipaque increased, but β-CD-(PCL-b-PAEMA-b-PPEGMA)$_{21}$/Au/DOX had higher HU values than Omnipaque at the same concentrations, indicating that the gold nanoparticles provide high CT imaging efficiency for mice implanted with tumor cells.

The above described embodiments are preferred embodiments of the present invention, but the embodiments of the invention are not limited by the foregoing embodiments. Other changes, modifications, substitutions, combinations, and simplification made without departing from the spirit or score of the present invention are also possible, all of which are explicitly contemplated and made part of this disclosure.

What is claimed is:

1. An amphipathic pH-responsive β-cyclodextrin-based star-shaped polymer with the structure represented by the following formula (I):

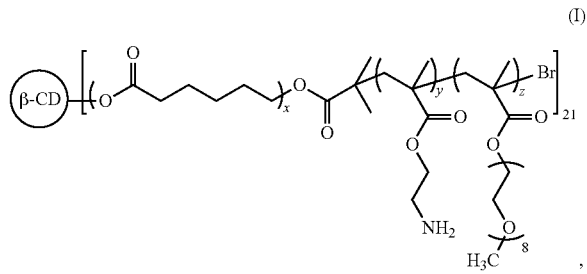

(I)

wherein x=4-15, y=3-20, z=10-30.

2. A method for preparing the amphipathic pH-responsive β-cyclodextrin-based star-shaped polymer according to claim 1, comprising:
   (1) preparation of a pH-responsive monomer precursor (tBAM), wherein tert-butyl N-(2-hydroxyethyl)carbamate, N,N-diisopropylethylamine are mixed in a solvent, and methacryloyl chloride is added under ice bath condition; the reaction is carried out under ice bath condition and subsequently at room temperature to obtain the precursive pH-responsive monomer t-butyl methacrylate-2-carbamate (tBAM);
   (2) preparation of a polymer containing polycaprolactone β-CD-(PCL-OH)$_{21}$, wherein β-CD, ε-CL and a catalyst are mixed and heated to react, so as to obtain the polymer β-CD-(PCL-OH)$_{21}$;
   (3) preparation of a macroinitiator β-CD-(PCL-Br)$_{21}$, wherein the β-CD-(PCL-OH)$_{21}$ prepared in step (2) is dissolved in a solvent; triethylamine (TEA) and initiator 2-bromoisobutyryl bromide (BIBB) are then added under ice bath; the reaction is carried out under ice bath condition and subsequently at room temperature to obtain the macroinitiator β-CD-(PCL-Br)$_{21}$;

(4) preparation of a pH-responsive polymer precursor β-CD-(PCL-b-PtBAM)$_{21}$: the macroinitiator β-CD-(PCL-Br)$_{21}$ prepared in step (3), the precursor tBAM prepared in step (1) and a catalyst are dissolved in a solvent, after which a ligand 1,1,4,7,10,10-hexamethyltriethylenetetramine (HMTETA) is further added; then a reducing agent is introduced and the solution is heated to react to obtain the pH-responsive polymer β-CD-(PCL-b-PtBAM)$_{21}$;

(5) preparation of an amphipathic star-shaped polymer β-CD-(PCL-b-tBAM-b-PPEGMA)$_{21}$, wherein the pH-responsive polymer precursor β-CD-(PCL-b-PtBAM)$_{21}$ prepared in step (4), poly(ethylene glycol) methyl ether methacrylate (PEGMA), a ligand 1,1,4,7,10,10-hexamethyltriethylenetetramine (HMTETA) and a catalyst are dissolved in a solvent; after mixing homogeneously, a reducing agent is added and the solution is heated to react to obtain the amphipathic star-shaped polymer β-CD-(PCL-b-tBAM-b-PPEGMA)$_{21}$;

(6) preparation of an amphipathic pH-responsive β-cyclodextrin-based star-shaped polymer β-CD-(PCL-b-PAEMA-b-PPEGMA)$_{21}$, wherein the amphiphilic star-shaped polymer prepared in step (5) is dissolved in a solvent, and after addition of trifluoroacetic acid (TFA), the reaction is carried out under ice bath condition and subsequently at room temperature to obtain the amphipathic pH-responsive O-cyclodextrin-based star-shaped polymer β-CD-(PCL-b-PAEMA-b-PPEGMA)$_{21}$.

3. The method for preparing the amphipathic pH-responsive β-cyclodextrin-based star-shaped polymer according to claim 2, wherein the molar parts of the reactants in step (1) are:

| | |
|---|---|
| tert-butyl N-(2-hydroxyethyl)carbamate | 1 |
| N,N-diisopropylethylamine | 1-3 |
| methacryloyl chloride | 1-3 | the molar parts of the reactants in step (2) are:

| | |
|---|---|
| β-CD | 1 |
| ε-CL | 84-315 | the molar parts of the reactants in step (3) are:

| | |
|---|---|
| β-CD-(PCL-OH)$_{21}$ | 1 |
| TEA | 21-84 |
| BIBB | 21-84 | the molar parts of the reactants in step (4) are:

| | |
|---|---|
| macroinitiator (β-CD-(PCL-Br)$_{21}$) | 1 |
| tBAM | 63-420 |
| HMTETA | 8-12 | the molar parts of the reactants in step (5) are:

| | |
|---|---|
| pH-responsive polymer precursor | 1 |
| PEGMA | 210-630 |
| HMTETA | 8-12 | the molar parts of the reactants in step (6) are:

| | |
|---|---|
| amphipathic star-shaped polymer | 1 |
| TFA | 30-60. |

4. The method for preparing the amphipathic pH-responsive β-cyclodextrin-based star-shaped polymer according to claim 2, wherein, in step (1), the reaction is carried out under ice bath condition for 0.5-4 h, and subsequently at room temperature for 24-48 h.

5. The method for preparing the amphipathic pH-responsive β-cyclodextrin-based star-shaped polymer according to claim 2, wherein: in step (2) the solution is heated to 90-130° C. to react for 24-48 h; in step (3) the reaction is carried out under ice bath condition for 4-6 h, and subsequently at room temperature for 24-48 h; in step (4) the solution is heated to 60-90° C. to react for 24-48 h; in step (5) the solution is heated to 60-90° C. to react for 48-96 h; in step (6) the reaction is carried out under ice bath condition for 0.5-4 h, and subsequently at room temperature for 4-10 h.

6. A unimolecular micelle system comprising the amphipathic pH-responsive star-shaped polymer according to claim 1, wherein the micelle system is obtained by dissolving the amphiphilic pH-responsive β-cyclodextrin-based star-shaped polymer as claimed in claim 1 in a solvent.

7. A method of loading water-insoluble drug(s) comprising the steps of: dissolving a water-insoluble drug in an organic solvent, mixing the unimolecular micelle system of claim 6 with the water-insoluble drug solution, stirring homogeneously, and dialyzing to obtain a water-insoluble-drug-loaded micelle system.

8. A gold-nanoparticles (AuNPs)-loaded composite material based on the amphipathic pH-responsive β-cyclodextrin-based star-shaped polymer unimolecular micelle system according to claim 6, wherein after the amphiphilic pH-responsive β-cyclodextrin-based star-shaped polymer and the water-soluble gold salt are respectively dissolved in the same solvent, the amphiphilic pH-responsive β-cyclodextrin-based star-shaped polymer solution and the water-soluble gold salt solution are mixed and stirred to obtain an AuNPs-loaded composite material.

9. A method for CT imaging a patient in need thereof, comprising administering to the patient the AuNPs-loaded composite material of claim 8.

10. A method of loading water-insoluble drug(s) comprising the steps of: dissolving a water-insoluble drug in an organic solvent, mixing the AuNPs-loaded composite material of claim 8 with the water-insoluble drug solution, stirring homogeneously, and dialyzing to obtain a water-insoluble-drug-loaded micelle system.

* * * * *

UNITED STATES PATENT AND TRADEMARK OFFICE
CERTIFICATE OF CORRECTION

PATENT NO. : 10,874,609 B2
APPLICATION NO. : 16/080355
DATED : December 29, 2020
INVENTOR(S) : Lijuan Zhang et al.

Page 1 of 1

It is certified that error appears in the above-identified patent and that said Letters Patent is hereby corrected as shown below:

On the Title Page

Column 1, Assignee, Line 1, after "Technology" insert -- , (CN) --

In the Specification

Column 1, Line 6, Above "FIELD OF THE INVENTION" insert
-- CROSS-REFERENCES TO RELATED APPLICATIONS
This application is the United States national phase of International Application No. PCT/CN2016/109907 filed Dec. 14, 2016, and claims priority to Chinese Patent Application No. 201610210456.X filed Apr. 5, 2016, the disclosures of each of which are hereby incorporated by reference in their entireties.
BACKGROUND OF THE INVENTION --

Column 1, Line 17, delete "BACKGROUND OF THE ART" and insert -- Description of Related Art --

In the Claims

Column 21, Line 28, Claim 2, delete "O-cyclodextrin-based" and insert -- β-cyclodextrin-based --

Signed and Sealed this
First Day of June, 2021

Drew Hirshfeld
*Performing the Functions and Duties of the*
*Under Secretary of Commerce for Intellectual Property and*
*Director of the United States Patent and Trademark Office*